(12) United States Patent
Pang et al.

(10) Patent No.: US 12,365,599 B2
(45) Date of Patent: Jul. 22, 2025

(54) NANOCRYSTALS

(71) Applicant: QUANTUM SCIENCE LTD, Warrington (GB)

(72) Inventors: Hao Pang, Trafford (GB); Jie Li, Stockport (GB)

(73) Assignee: QUANTUM SCIENCE LTD, Warrington (GB)

( * ) Notice: Subject to any disclaimer, the term of this patent is extended or adjusted under 35 U.S.C. 154(b) by 818 days.

(21) Appl. No.: 17/442,344

(22) PCT Filed: Mar. 25, 2020

(86) PCT No.: PCT/EP2020/058346
§ 371 (c)(1),
(2) Date: Sep. 23, 2021

(87) PCT Pub. No.: WO2020/193623
PCT Pub. Date: Oct. 1, 2020

(65) Prior Publication Data
US 2022/0169527 A1    Jun. 2, 2022

(30) Foreign Application Priority Data
Mar. 25, 2019 (GB) ..................... 1904069

(51) Int. Cl.
C01G 21/20 (2006.01)
C01B 19/00 (2006.01)
(Continued)

(52) U.S. Cl.
CPC ............ *C01G 21/20* (2013.01); *C01B 19/007* (2013.01); *C01G 21/08* (2013.01); *C01G 21/10* (2013.01);
(Continued)

(58) Field of Classification Search
CPC ........ C01G 21/00; C01G 21/08; C01G 21/10; C01G 21/20; G01S 17/894; G01S 7/4816;
(Continued)

(56) References Cited

U.S. PATENT DOCUMENTS

2013/0048922 A1    2/2013  Zhou et al.
2018/0127852 A1*   5/2018  Clarke ...................... C25B 1/22
2019/0006541 A1*   1/2019  So ........................... C30B 29/46

FOREIGN PATENT DOCUMENTS

CN    1997778 A    7/2007
CN    103413892 A  11/2013
(Continued)

OTHER PUBLICATIONS

Zaiats, Gary, et al. "PbSe/CdSe thin-shell colloidal quantum dots." Zeitschrift für Physikalische Chemie 229.1-2 (2015): 3-21.*
(Continued)

*Primary Examiner* — Richard M Rump
(74) *Attorney, Agent, or Firm* — Birch, Stewart, Kolasch & Birch, LLP

(57) ABSTRACT

The present invention provides the use of a lead (IV) containing compound to prepare a lead chalcogenide nanocrystal and a method for producing broadband lead chalcogenide nanocrystals in a low cost, size-controllable and scalable method, the method comprising contacting a lead (IV) containing compound with an organic acid and a chalcogen-containing reagent.

25 Claims, 13 Drawing Sheets

(51) Int. Cl.
*C01G 21/08* (2006.01)
*C01G 21/10* (2006.01)
*G01S 7/481* (2006.01)
*G01S 17/894* (2020.01)
*B82Y 5/00* (2011.01)
*B82Y 15/00* (2011.01)
*B82Y 20/00* (2011.01)
*B82Y 40/00* (2011.01)
*G01N 1/30* (2006.01)
*G01N 33/58* (2006.01)

(52) U.S. Cl.
CPC .......... *G01S 7/4816* (2013.01); *G01S 17/894* (2020.01); *B82Y 5/00* (2013.01); *B82Y 15/00* (2013.01); *B82Y 20/00* (2013.01); *B82Y 40/00* (2013.01); *C01P 2004/64* (2013.01); *C01P 2006/60* (2013.01); *G01N 1/30* (2013.01); *G01N 33/587* (2013.01)

(58) Field of Classification Search
CPC .......... B82Y 5/00; B82Y 15/00; B82Y 30/00; B82Y 40/00; B82Y 20/00; C01P 2004/64; C01P 2006/60; G01N 1/30; G01N 33/587; C01B 19/007
See application file for complete search history.

(56) References Cited

FOREIGN PATENT DOCUMENTS

| | | |
|---|---|---|
| CN | 108483412 A | 9/2018 |
| CN | 109294586 A | 2/2019 |
| JP | 2013-525244 A | 6/2013 |
| JP | 2018-529214 A | 10/2018 |
| WO | WO 2005/106082 A1 | 11/2005 |
| WO | WO 2017/039774 A2 | 3/2017 |

OTHER PUBLICATIONS

Yanover, Diana, et al. "Small-sized PbSe/PbS core/shell colloidal quantum dots." Chemistry of Materials 24.22 (2012): 4417-4423.*
Japanese Office Action for Japanese Application No. 2021-560175, dated Jan. 30, 2024.
Lei et al., "Weathering of Rock Carvings and Their Protective Materials," Materials Report A: Reviews, vol. 26, Issue 8, Aug. 2012, pp. 88-92 (21 pages total), with English translation.
Cademartiri et al., "Multigram Scale, Solventless, and Diffusion-Controlled Route to Highly Monodisperse PbS Nanocrystals," The Journal of Physical Chemistry B Letters, vol. 110, No. 2, 2006 (Published on Dec. 22, 2005), pp. 671-673.
Hendricks et al., "A tunable library of substituted thiourea precursors to metal sulfide nanocrystals." Nanomaterials, Science (sciencemag. org), vol. 348, No. 6240, Jun. 12, 2015 (Corrected Jun. 16, 2015), pp. 1226-1230.
Hines et al., "Colloidal PbS Nanocrystals with Size-Tunable Near-Infrared Emission: Observation of Post-Synthesis Self-Narrowing of the Particle Size Distribution", Advanced Materials, vol. 15, No. 21, 2003 (Published on Sep. 16, 2003), pp. 1844-1849.
Liu et al., "Reduction of lead dioxide with oxalic acid to prepare lead oxide as the positive electrode material for lead acid batteries," RSC Advances, vol. 6. Nov. 3, 2016, pp. 108513-108522.
Chinese Office Action and Search Report for Chinese Application No. 202411206411.6, dated Mar. 1, 2025, with English translation.

* cited by examiner

NANOCRYSTALS

FIELD

The present invention relates in general to lead chalcogenide nanocrystals. In particular, the present invention relates to a method for producing lead chalcogenide nanocrystals using a lead (IV) containing compound. The present invention also extends to lead chalcogenide nanocrystals obtained by the method and to uses of the lead chalcogenide nanocrystals.

BACKGROUND

Nanocrystals are useful in a wide range of applications, for example because their optical properties can be finely tuned to provide the desired properties. The optical properties (for example light absorption and emission characteristics) of nanocrystals can be finely tuned by controlling their size. The largest nanocrystals produce the longest wavelengths (and lowest frequencies), while the smallest nanocrystals product shorter wavelengths (and higher frequencies). The size of the nanocrystals may be controlled by means of the method by which they are produced. This ability to finely tune the optical properties of the nanocrystals, by controlling their size, makes nanocrystals suitable for use in a wide range of applications, including, for example, photodetectors, sensors, solar cells, bio-imaging and bio-sensing, photovoltaics, displays, lighting, security and counterfeiting, batteries, wired high-speed communications, quantum dot (QD) lasers, photocatalysts, spectrometers, injectable compositions, field-effect transistors, light-emitting diodes, lasers, photonic or optical switching devices, hydrogen production and metamaterials.

Lead nanocrystals are known, as are various methods for producing them. For example, Hines et al., Adv. Mater. 2003, 15, No. 21, 1844-1849 discloses a method for preparing lead-sulphide nanocrystals that have bandgaps that are tuneable throughout the near-infrared (for example 800 to 1800 nm). The lead-sulphide nanocrystals may be prepared by reacting lead (II) oxide (PbO) with oleic acid to form lead oleate, which is then reacted with bis(trimethylsilyl)sulphide. However, the starting material lead (II) oxide is very expensive and the reaction described in Hines et al. was found to be difficult to control on a large scale. Thus, the method disclosed in Hines et al. is unsuitable for large scale production of lead nanocrystals.

Cademartiri et al., J. Phys. Chem. B., vol. 110, no. 2, 2006, 671-673 discloses a method for preparing lead-sulphide nanocrystals in which lead chloride ($PbCl_2$) is reacted with oleylamine and elemental sulphur. The nanocrystals obtained by this method were difficult to purify and demonstrated a limited peak absorption of 1245 to 1625 nm. Residual lead chloride remaining on the lead-sulphide nanocrystals typically precipitates over long periods of time, making it difficult to produce highly pure lead-sulphide nanocrystals from lead chloride. Thus, the method disclosed in Cademartiri et al. is unsuitable for producing pure and highly monodispersed lead-sulphide nanocrystals on a large scale.

Hendricks et al., Science, 2015, 348, 1226-1230 discloses a method for preparing lead-sulphide nanocrystals in which lead oleate is reacted with a reactive disubstituted thiourea. The lead-sulphide nanocrystals prepared by this method exhibited an absorption peak of 850 to 1800 nm. This method is complex to conduct on a large scale as the size (and absorption) of the nanocrystals is controlled by altering the side chains of the thiourea reactants.

Thus, whilst several methods for producing lead chalcogenide nanocrystals are known, these methods fail to allow for ready control of crystal size and therefore the fine tuning of the optical properties of the nanocrystals. The known methods also typically fail to provide nanocrystals exhibiting a broad absorption range. Additionally, the known methods are unsuitable for preparing lead chalcogenide nanocrystals on a large (for example commercially useful) scale.

There is, therefore, a desire to find alternative methods for preparing lead chalcogenide nanocrystals that can be used on a large (for example commercially useful) scale and/or that enable the ready control of the size of the nanocrystals prepared so as to enable fine tuning of the optical properties of the nanocrystals. It is also desired to provide methods that provide lead chalcogenide nanocrystals that exhibit a broad absorption range. It is believed that such a method would provide lead chalcogenide nanocrystals that are suitable for use in a wide range of applications.

SUMMARY

According to a first aspect of the present invention there is provided the use of a lead (IV) containing compound to prepare a lead chalcogenide nanocrystal or a lead chalcogenide nanocrystal composition.

According to a second aspect of the present invention, there is provided the use of lead (II, IV) oxide to prepare a lead chalcogenide nanocrystal or a lead chalcogenide nanocrystal composition.

According to a third aspect of the present invention, there is provided a method for preparing a lead chalcogenide nanocrystal or a lead chalcogenide nanocrystal composition, the method comprising contacting a lead (IV) containing compound with an organic acid and a chalcogen-containing reagent.

According to a fourth aspect of the present invention, there is provided method for preparing a lead chalcogenide nanocrystal or a lead chalcogenide nanocrystal composition, the method comprising contacting lead (II, IV) oxide with an organic acid and a chalcogen-containing reagent.

According to a fifth aspect of the present invention, there is provided a composition of lead chalcogenide nanocrystals obtained by the method according to the third or fourth aspect of the present invention.

According to a sixth aspect of the present invention, there is provided a film comprising the composition of nanocrystals according to the fifth aspect of the present invention.

According to a seventh aspect of the present invention, there is provided a system or composition, such as a photodetector, sensor, solar cell, bio-imaging or bio-sensing composition, photovoltaic system, display, battery, laser, photocatalyst, spectrometer, injectable composition, field-effect transistor, light-emitting diode, photonic or optical switching device, or metamaterial comprising the composition according to the fifth aspect of the present invention.

According to an eighth aspect of the present invention, there is provided a lead chalcogenide nanocrystal composition, said nanocrystals having a mean particle size in the range of 2 to 20 nm, and a relative size dispersion of less than 25%.

The nanocrystal compositions according to the eighth aspect of the invention preferably exhibit absorption wavelength in the range of 500 to 4500 nm, preferably suitably in the range of 500 to 2400 nm.

The nanocrystal compositions according to the eighth aspect of the invention preferably exhibit emission wavelength in the range of 600 to 4500 nm, preferably suitably in the range of 600 to 2500 nm.

The nanocrystal compositions according to the eighth aspect of the invention preferably exhibit absorption full width at half maximum (FWHM) values of less than 250 nm, preferably less than 230 nm, preferably less than 130 nm, preferably less than 110 nm. Preferably, the FWHM range is in the range of 10-250 nm, preferably 20-220 nm, preferably 50-150 nm, preferably 75-115 nm, preferably 80-110 nm.

The nanocrystal compositions according to the eighth aspect of the invention preferably exhibit emission full width at half maximum (FWHM) values of less than 250 nm, preferably less than 230 nm, preferably less than 150 nm, preferably less than 110 nm. Preferably, the FWHM range is in the range of 10-250 nm, preferably 20-220 nm, preferably 30-150 nm, preferably 40-110 nm.

The nanocrystal compositions according to the eighth aspect of the invention preferably exhibit quantum yield (QY) values of greater than 10%, preferably greater than 20%, preferably greater than 40%, preferably greater than 50%.

According to the first to eighth aspects of the invention, preferably the lead chalcogenide nanocrystal or a lead chalcogenide nanocrystal composition comprises PbS, PbSe, PbTe or mixtures thereof, more preferably PbS or PbSe, most preferably PbS.

DESCRIPTION

When describing the aspects of the invention, the terms used are to be construed in accordance with the following definitions, unless a context dictates otherwise.

As used in the specification and the appended claims, the singular forms "a", "an," and "the" include both singular and plural referents unless the context clearly dictates otherwise. By way of example, "a nanocrystal" means one nanocrystal or more than one nanocrystal. By way of example, "a lead (IV) containing compound" means one lead (IV) containing compound or more than one lead (IV) containing compound. References to a number when used in conjunction with comprising language include compositions comprising said number or more than said number.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

As used herein, unless otherwise expressly specified, all numbers such as those expressing values, ranges, amounts of percentages may be read as if prefaced by the word "about", even if the term does not expressly appear.

The term "about" as used herein when referring to a measurable value such as a parameter, an amount, a temporal duration, and the like, indicates that a value includes the standard deviation of error for the device or method being employed to determine the value. The term "about" is meant to encompass variations of +1-10% or less, +/−5% or less, or +/−0.1% or less of and from the specified value, insofar such variations are appropriate to perform in the disclosure. It is to be understood that the value to which the modifier "about" refers is itself also specifically disclosed.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Unless otherwise defined, all terms used in the disclosure, including technical and scientific terms, have the meaning as commonly understood by one of ordinary skill in the art to which this disclosure belongs. By means of further guidance, definitions for the terms used in the description are included to better appreciate the teaching of the present disclosure. All publications referenced herein are incorporated by reference thereto.

As used herein, unless otherwise defined, the term "composition" may be open ended or closed. For example, "composition" comprises the specified material, i.e., the nanocrystals, and further unspecified material, or may consist of the specified material, i.e., to the substantial exclusion of non-specified materials.

Suitable features of the invention are now set forth.

Use

According to a first aspect, the present invention provides the use of a lead (IV) containing compound to prepare a lead chalcogenide nanocrystal or a composition of lead chalcogenide nanocrystals.

As used herein, the term "lead (IV) containing compound" means any compound that includes lead in an oxidation state of +4. Any suitable such compound may be used. Examples of suitable lead (IV) containing compounds include, but are not limited to, lead (II, IV) oxide (i.e. $Pb_3O_4$) and lead (IV) oxide (i.e. $PbO_2$).

Suitably, the lead (IV) containing compound may comprise lead (II, IV) oxide or lead (IV) oxide, or a combination thereof. Suitably, the lead (IV) containing compound may comprise lead (II, IV) oxide.

The use of lead (II, IV) oxide is advantageous because it is a highly reactive and inexpensive material that can be readily used in large scale (such as commercial) processes, i.e. in an industrial scale production process.

As used herein, the term "chalcogenide" means a chemical compound that contains at least one chalcogen and at least one electropositive element. As used herein, the term "chalcogen" means a group 16 element. For example, a "chalcogenide" may comprise a chemical compound that contains oxide, sulphide, selenide, telluride or polonide and at least one electropositive element or cation. A "lead chalcogenide" is a chemical compound that contains oxide, sulphide, selenide, telluride or polonide and at least one lead cation.

As used herein, the term "nanocrystal" means a crystalline particle with at least one dimension measuring less than 100 nanometres (nm).

The lead chalcogenide nanocrystal may comprise a quantum dot (QD) or consist of quantum dots (QDs). As used herein, by the term "quantum dot" we mean a semiconductor nanocrystal exhibiting quantum confinement effects that allow it to mimic the properties of an atom. Quantum dots may also be known as zero-dimensional nanocrystals.

According to a second aspect, the present invention provides the use of lead (II, IV) oxide to prepare a lead chalcogenide nanocrystal.

Suitably, the lead chalcogenide nanocrystals or lead chalcogenide nanocrystal composition prepared from lead (IV) containing compounds exhibit absorption in the visible and near infra-red ranges, suitably in the range of 500 to 4500 nm, preferably suitably in the range of 500 to 2400 nm.

Suitably, lead sulphide nanocrystals or lead sulphide nanocrystal compositions prepared from lead (IV) containing compounds exhibit absorption in the visible and near infra-red ranges, suitably in the range of 500 to 2400 nm.

Suitably, lead selenide nanocrystals or lead selenide nanocrystal compositions prepared from lead (IV) containing compounds exhibit absorption in the visible and near infra-red ranges, suitably in the range of 800 to 4500 nm.

Suitably, lead telluride nanocrystals or lead telluride nanocrystal compositions prepared from lead (IV) containing compounds exhibit absorption in the visible and near infra-red ranges, suitably in the range of 500 to 2400 nm.

Suitably, the lead chalcogenide nanocrystals or lead chalcogenide nanocrystal composition prepared from lead (IV) containing compounds exhibit emission in the visible and near infra-red ranges, suitably in the range of 600 to 4500 nm, preferably suitably in the range of 600 to 2500 nm.

Suitably, lead sulphide nanocrystals or lead sulphide nanocrystal compositions prepared from lead (IV) containing compounds exhibit emission in the visible and near infra-red ranges, suitably in the range of 600 to 2500 nm.

Suitably, lead selenide nanocrystals or lead selenide nanocrystal compositions prepared from lead (IV) containing compounds exhibit emission in the visible and near infra-red ranges, suitably in the range of 900 to 4500 nm.

Suitably, lead telluride nanocrystals or lead telluride nanocrystal compositions prepared from lead (IV) containing compounds exhibit emission in the visible and near infra-red ranges, suitably in the range of 600 to 2500 nm.

Method

According to a third aspect, the present invention provides a method for preparing a lead chalcogenide nanocrystal or lead chalcogenide nanocrystal composition, the method comprising contacting a lead (IV) containing compound with an organic acid and a chalcogen-containing reagent.

A fourth aspect of the present invention provides a method for preparing a lead chalcogenide nanocrystal or lead chalcogenide nanocrystal composition, the method comprising contacting lead (II, IV) oxide with an organic acid and a chalcogen-containing reagent The method suitably prepares a plurality of lead chalcogenide nanocrystals, i.e., a nanocrystal composition. The lead chalcogenide nanocrystals prepared by the method of the invention may comprise quantum dots (i.e. crystalline quantum dots).

Various aspects of the methods of the invention, such as the particular reagents and/or reaction conditions, may be varied so as to provide lead chalcogenide nanocrystals of a desired size so as to achieve desired optical properties, such as desired absorption and emission (for example for a particular use of the nanocrystals).

For example, the reagents used (particularly chalcogen-containing reagent) in the methods may be varied to provide lead chalcogenide nanocrystals of a desired size so as to achieve desired optical properties, such as desired absorption and emission (for example for a particular use of the nanocrystals).

For example, the reaction conditions of the methods may be varied to provide lead chalcogenide nanocrystals of a desired size so as to achieve desired optical properties, such as desired absorption and emission (for example for a particular use of the nanocrystals).

In other words, the uses and methods of the invention may be used to prepare lead chalcogenide nanocrystals having size-tuneable optical properties. Examples of the reagents and/or reaction conditions that may be varied are discussed herein.

The method of the invention may comprise the step of selecting a particular reagent so as to control the size of the nanocrystal(s) prepared, i.e. so as to prepare nanocrystal(s) having desired optical properties. For example, a reagent that may be selected in order to control the size of the nanocrystals prepared may be the particular chalcogen-containing reagent The method of the invention may comprise the step of modifying a reaction condition so as to control the size of the nanocrystal(s) prepared, i.e. so as to prepare nanocrystal(s) having desired optical properties. For example, reaction conditions that may be modified in order to control the size of the nanocrystals prepared include one or more of the following:
(i) solvent type;
(ii) amount of solvent;
(iii) organic acid type;
(iv) amount of organic acid;
(v) mode of addition of the reactants (particularly of chalcogen-containing reagent);
(vi) reaction temperature;
(vii) reaction time;
(viii) ratio of Pb to chalcogen-containing reagent; and
(ix) addition of a secondary solvent.

By modifying a reaction condition to control the size of the nanocrystal(s) prepared, the optical properties (absorption and emission) may be modified and finely tuned to the desired properties. This provides a method for finely tuning the size and optical properties (absorption and emission) of the nanocrystals.

Suitably, the method of the invention provides lead chalcogenide nanocrystals and compositions thereof exhibiting absorption in the visible and near infra-red ranges, for example in a range of from about 500 to 4500 nm, preferably suitably in the range of 500 to 2400 nm. The particular absorption exhibited may be selected by varying the particular reagents and/or reaction conditions used as discussed herein. Suitably, lead sulphide nanocrystals prepared from lead (IV) containing compounds exhibit absorption in the visible and near infra-red ranges, suitably in the range of 500 to 2400 nm. Suitably, lead selenide nanocrystals prepared from lead (IV) containing compounds exhibit absorption in the visible and near infra-red ranges, suitably in the range of 800 to 4500 nm. Suitably, lead telluride nanocrystals prepared from lead (IV) containing compounds exhibit absorption in the visible and near infra-red ranges, suitably in the range of 500 to 2400 nm.

Suitably, the method of the invention provides lead chalcogenide nanocrystals and compositions thereof exhibiting emission in the visible and near infra-red ranges, for example in a range of from about 600 to 4500 nm, preferably suitably in the range of 600 to 2500 nm. The particular emission exhibited may be selected by varying the particular reagents and/or reaction conditions used as discussed herein.

Suitably, lead sulphide nanocrystals prepared from lead (IV) containing compounds exhibit emission in the visible and near infra-red ranges, suitably in the range of 600 to 2500 nm. Suitably, lead selenide nanocrystals prepared from lead (IV) containing compounds exhibit emission in the visible and near infra-red ranges, suitably in the range of 900 to 4500 nm. Suitably, lead telluride nanocrystals prepared from lead (IV) containing compounds exhibit emission in the visible and near infra-red ranges, suitably in the range of 600 to 2500 nm.

Suitably, as for the uses discussed above, any suitable lead (IV) containing compound may be used in the method of the invention. Suitably, the lead (IV) containing compound may comprise lead (II, IV) oxide or lead (IV) oxide, or a combination thereof. Suitably, the lead (IV) containing compound may comprise lead (II, IV) oxide.

As used herein, the term "organic acid" means an organic compound having acidic properties. As used herein, the term "organic compound" means a chemical compound in which one or more atoms of carbon are covalently linked to atoms of other elements, most commonly hydrogen, oxygen, and/or nitrogen.

Any suitable organic acid may be used in the method of the present invention. Suitably, the organic acid comprises a carboxylic acid, such as a fatty acid (for example a saturated or unsaturated fatty acid, suitably an unsaturated fatty acid). Examples of suitable carboxylic acids include C4 to C28, such as C12-C22, fatty acids. Suitably, the organic acid may comprise oleic acid.

Suitably, the organic acid comprises a fatty acid, preferably oleic acid.

As used herein, the term "chalcogen-containing reagent" means a reagent that comprises at least one chalcogen, i.e. at least one group 16 element or anion thereof. Any suitable chalcogen-containing reagent may be used in the method of the invention. For example, the chalcogen-containing reagent may be selected from an oxygen-, sulphur-, selenium- and tellurium-containing reagent (such as a sulphur-, selenium- and tellurium-containing reagent, particularly a sulphur- or selenium containing reagent), and mixtures thereof.

Suitably, the chalcogen-containing reagent may comprise a chalcogen-containing compound or an elemental chalcogen, and mixtures thereof. For example, the chalcogen-containing reagent may comprise a chalcogen-containing compound. For example, the chalcogen-containing reagent may comprise an elemental chalcogen.

A suitable chalcogen-containing compound may comprise an oxygen, sulphur, selenium or tellurium atom, or a combination thereof, and at least one suitable atom of another element. More suitably, the chalcogen-containing compound may comprise a sulphur, selenium or tellurium atom, or a combination thereof (preferably a sulphur or selenium atom), and at least one suitable atom of another element.

Suitably, the chalcogen-containing compound may comprise an ionic compound comprising an oxygen, sulphur, selenium or tellurium anion, or a combination thereof, and at least one suitable cation. More suitably, the chalcogen-containing ionic compound may comprise a sulphur, selenium or tellurium anion, or a combination thereof (preferably a sulphur or selenium anion), and at least one suitable cation.

Examples of suitable oxygen-containing reagents include oxygen gas.

Examples of suitable sulphur-containing reagents include bis(trialkylsilyl)sulphide compounds (such as bis(trimethylsilyl)sulphide, bis(triethylsilyl)sulphide and bis(tripropylsilyl)sulphide, particularly bis(trimethylsilyl)sulphide), thioacetamide, tri-n-octylphosphine sulphide, tributylphosphine sulphide, (alkyl substituted, phenyl) thiourea compounds (such as N,N'-disubstituted and N,N,N'-trisubstituted thioureas), alkyl substituted thioamide compounds and elemental sulphur.

Thioacetamide is an inexpensive reagent which has a low toxicity, making it particularly suitable for large scale use.

Examples of suitable selenium-containing compounds include bis(trimethylsilyl)selenide, tri-n-octylphosphine selenide (TOPSe) and tributylphosphine selenide.

It is also preferable to use certain phosphine containing reagents, as these can form higher reactive Se precursors than TOPSe. These precursors play an important role in maintaining a high PbSe oversaturation which is important in promoting nucleation, growth and to control size distribution of QDs as well as allows mild reaction conditions. Examples of preferred phosphine containing reagents include diphenylphosphine selenide (DPP), di-ortho-tolylphosphine selenide (DOTP) and diphenylphosphineoxide selenide (DPPO).

Examples of suitable tellurium-containing compounds include tri n-octylphosphine telluride.

For example, the method of the present invention may comprise contacting lead (II, IV) oxide with a fatty acid and a chalcogen-containing reagent.

For example, the method of the present invention may comprise contacting lead (II, IV) oxide with oleic acid and a chalcogen-containing reagent.

For example, the method of the present invention may comprise contacting lead (II, IV) oxide with a fatty acid and a chalcogen-containing compound.

For example, the method of the present invention may comprise contacting lead (II, IV) oxide with oleic acid and a chalcogen-containing compound.

For example, the method of the present invention may comprise contacting lead (II, IV) oxide with a fatty acid and an oxygen, sulphur, selenium or tellurium-containing (such as a sulphur, selenium or tellurium-containing, particularly a sulphur-containing or a selenium-containing) reagent.

For example, the method of the present invention may comprise contacting lead (II, IV) oxide with oleic acid and an oxygen, sulphur, selenium or tellurium-containing (such as a sulphur, selenium or tellurium-containing, particularly a sulphur-containing or a selenium-containing) reagent.

For example, the method of the present invention may comprise contacting lead (II, IV) oxide with a fatty acid and an oxygen, sulphur, selenium or tellurium-containing (such as a sulphur, selenium or tellurium-containing, particularly a sulphur-containing or a selenium-containing) compound.

For example, the method of the present invention may comprise contacting lead (II, IV) oxide with oleic acid and an oxygen, sulphur, selenium or tellurium-containing (such as a sulphur, selenium or tellurium-containing, particularly a sulphur-containing or a selenium-containing) compound.

The references to contacting the lead (IV) containing compound with an organic acid and a chalcogen-containing reagent refer to bringing these reagents together in such a way as to enable them to react, i.e. to prepare lead chalcogenide nanocrystals and/or compositions thereof.

Suitably, the lead (IV) containing compound is contacted with the organic acid to produce a lead salt and the lead salt is contacted with the chalcogen-containing reagent. In other words, the lead (IV) containing compound is contacted with and reacts with the organic acid to form a lead salt. The lead salt so formed then reacts with the chalcogen-containing reagent to form the lead chalcogenide nanocrystal(s) and/or compositions thereof. The lead salt may be isolated before reaction with the chalcogen-containing reagent, although typically it is unnecessary to do so.

Conducting the method without isolating the lead salt offers the advantage of conducting the method as a one-pot synthesis, which enables easy scale up of the method.

The formation of a lead salt as discussed above may be monitored in any suitable way, for example visually by means of a colour change as the lead salt is formed.

The lead (IV) containing compound, organic acid and chalcogen-containing reagent may be contacted (or reacted) in any suitable manner, typically by mixing in a suitable reaction vessel.

Typically, the lead (IV) containing compound is believed to react with the organic acid to form a lead salt, which lead salt then reacts with the chalcogen-containing reagent to form the lead chalcogenide nanocrystal(s) and/or compositions thereof.

Typically, the lead (IV) containing compound may be contacted with a molar excess of the organic acid. For example, the molar ratio of the lead atoms (in the lead(IV) containing compound) to the organic acid may be in the range of from 1:1.5 to 1:200, such as from 1:1.5 to 1:60. It is believed that the molar ratio of the lead atoms (in the lead (IV) containing compound) to organic acid may be selected so as to achieve a desired nanocrystal size, and so a desired absorption. Typically, the higher the amount of organic acid that is used then the larger the nanocrystals are formed.

Typically, the lead salt may be contacted with the chalcogen-containing reagent in an amount such that there is a molar excess of lead atoms to chalcogen atoms. For example, the molar ratio of lead atoms to chalcogen atoms may be in the range of from 0.9:1 to 50:1; such as from 1.5:1 to 30:1, such as from 1.5:1 to 25:1. It is believed that the molar ratio of the lead atoms (in the lead salt) to chalcogen atoms (in the chalcogen-containing reagent) may be selected so as to achieve a highly monodispersed nanocrystals over a wide range of sizes, and consequently a desired narrow absorption peak over a wider range. Typically, the higher the amount of lead atoms used then the highly monodispersed nanocrystals over a wider absorption range are formed.

Typically, the lead (IV) containing compound and the organic acid are mixed in a suitable solvent until the reaction (i.e. the formation of a lead salt) is substantially complete and a solution of the lead salt in the solvent is produced. The chalcogen-containing reagent may then be added to the solution of the lead salt and allowed to react to form the lead chalcogenide nanocrystals and/or compositions thereof. The chalcogen-containing reagent may be added with or without solvent.

The lead salt and chalcogen-containing reagent may be contacted in any suitable way. Suitably, the lead salt and the chalcogen-containing reagent may be mixed together, for example in the presence of a suitable solvent. A solution of the chalcogen-containing reagent in a suitable solvent may, for example, be added to a solution of the lead salt in a suitable solvent (preferably the same solvent). Alternatively, the chalcogen-containing reagent may, for example, be added directly to a solution of the lead salt in a suitable solvent. The addition of the chalcogen-containing reagent may be conducted in one step or in multiple steps. For example, the chalcogen-containing reagent may be added to the lead salt in two or more portions, for example in two portions. It is believed that the mode of addition of the chalcogen-containing reagent may be used to change the size of the nanocrystals produced and therefore to finely tune the optical properties of the nanocrystals. Typically, adding the chalcogen-containing reagent in multiple steps provides larger nanocrystals (i.e. compared to a single step addition).

The method of the present invention may further comprise adding a second solvent immediately after the addition of the chalcogen-containing reagent to the lead salt (i.e. so as to rapidly quench the reaction). The second solvent is typically an organic solvent, such as polar solvent (for example acetone, methanol or ethanol) or a non-polar solvent (such as hexane).

The method of the present invention may be conducted at any suitable temperature. For example, the lead (IV) containing compound may be contacted with the organic acid at any suitable temperature, i.e. at any suitable temperature at which a reaction occurs. The particular temperature at which this reaction occurs may depend on the particular lead (IV) containing compound and organic acid being reacted. A suitable temperature may be in the range of from 120 to 250° C., for example from 120 to 240° C., for example from 180 to 240° C., for example from 180 to 230° C.

For example, when the lead (IV) containing compound comprises lead (II, IV) oxide and the organic acid comprises oleic acid, the temperature at which these are reacted (i.e. so as to form a lead salt) may be in the range of from 120 to 250° C., suitably from 120 to 240° C., suitably from 180 to 240° C., suitably from 180 to 230° C.

The lead salt may be contacted with the chalcogen-containing reagent at any suitable temperature, i.e. at any suitable temperature at which a reaction occurs. The particular temperature at which this reaction occurs may depend, inter alia, on the particular lead salt and chalcogen-containing reagent being reacted. A suitable temperature may be in the range of from 20 to 300° C. or 20 to 180° C. It is believed that the selection of a particular reaction temperature can be used to change the size of the nanocrystals formed, so as to finely tune their optical properties as desired. Typically, increasing the temperature at which the lead salt and the chalcogen-containing reagent are contacted/reacted provides larger nanocrystals.

The temperature at which the lead (IV) containing compound is contacted with the organic acid may be the same or different to the temperature at which the lead salt is contacted with the chalcogenide-containing reagent. Suitably, the temperature at which the lead (IV) containing compound is contacted with the organic acid may be higher than the temperature at which the resultant lead salt is contacted with the chalcogenide-containing reagent. For example, a temperature of 150-300° C. may be used for the resultant lead salt to contact with the chalcogenide-containing reagent to improve quality of quantum dots.

Suitably, the lead salt may be contacted with the chalcogen-containing reagent at a temperature of from 20 to 150° C., such as from 30 to 100° C., such as from 30 to 60° C., such as from 20 to 60° C., for example, about 40° C. Such a reaction temperature may be suitable when the chalcogen-containing reagent is bis(trimethylsilyl)sulphide, for example when the bis(trimethylsilyl)sulphide is contacted with lead oleate. Such low temperature conditions offer advantages in use, especially in relation to large scale production.

For example, when the lead salt comprises lead oleate and the chalcogen-containing reagent comprises bis(trimethylsilyl)sulphide, the temperature at which these are reacted may be in the range of from 20 to 180° C., such as from 20 to 55° C., preferably about 40° C. This method, in which the chalcogen-containing reagent comprises bis(trimethylsilyl) sulphide, may provide lead chalcogenide nanocrystals that exhibit absorption in the visible and near infra-red ranges, for example in a range of from about 500 to 2400 nm, such as from about 530 to 2400 nm, such as from about 530 to 1600 nm. This method, in which the chalcogen-containing reagent comprises bis(trimethylsilyl)sulphide, may provide lead chalcogenide nanocrystals that exhibit emission in the visible and near infra-red ranges, for example in a range of from about 600 to 2500 nm, such as from about 630 to 2500 nm, such as from about 630 to 1700 nm.

Suitably, the lead salt may be contacted with the chalcogen-containing reagent at a temperature of from 50 to 300° C., such as from 50 to 150° C. Such a reaction temperature may be suitable when the chalcogen-containing reagent comprises thioacetamide, for example when the thioacetamide is contacted with lead oleate. This method, in which the chalcogen-containing reagent comprises thioacetamide, may provide lead chalcogenide nanocrystals that exhibit absorption in the visible and near infra-red ranges, for example in a range of from about 500 to 2400 nm, such as 500 to 1700 nm. This method, in which the chalcogen-containing reagent comprises thioacetamide, may provide lead chalcogenide nanocrystals that exhibit emission in the visible and near infra-red ranges, for example in a range of from about 600 to 2500 nm, such as 600 to 1800 nm.

Suitably, the lead salt may be contacted with the chalcogen-containing reagent at a temperature of from 50 to 300° C., such as from 80 to 150° C. Such a reaction temperature may be suitable when the chalcogen-containing reagent comprises tri-n-octylphosphine selenide (TOPSe), for example when the TOPSe is contacted with lead oleate in presence of diphenylphosphine (DPP). This method, in which the chalcogen-containing reagent comprises TOPSe in presence of DPP, may provide lead chalcogenide nanocrystals that exhibit absorption in the visible and near infra-red ranges, for example in a range of from about 800 to 4500 nm, such as from about 900 to 4200 nm, such as from about 1100 to 4100 nm. This method, in which the chalcogen-containing reagent comprises TOPSe, may provide lead chalcogenide nanocrystals that exhibit emission in the visible and near infra-red ranges, for example in a range of from about 900 to 4500 nm, such as from about 1000 to 4300 nm, such as from about 1200 to 4100 nm.

The method of the present invention may be conducted in the presence of a solvent. Any suitable solvent may be used. Suitably, the solvent is a solvent that will not form a coordination complex with the lead. Suitably, the solvent is an organic solvent, such as a non-polar solvent or polar solvent, or a mixture thereof. Examples of suitable solvents include C4-C28 organic solvents, such as octadecene or polar solvents such as dimethylformamide, N-methyl-2-pyrrolidone, dimethylacetamide, tetrahydrofuran. Typically, the same solvent is used for the reaction of the lead (IV) containing compound with the organic acid, and for the reaction of the resultant lead salt with the chalcogen-containing reagent. This simplifies the method, making it particularly suitable for large scale use.

For example, the lead (IV) containing compound may be contacted with the organic acid in the presence of a suitable solvent. Suitably, the solvent is a non-polar solvent or a polar solvent or the mixture thereof. Examples of suitable solvents include C4-C22 organic solvents, such as octadecene.

For example, the resultant lead salt may be contacted with the chalcogen-containing reagent in the presence of a suitable solvent. Suitably, the solvent is a non-polar solvent or a polar solvent or the mixture thereof. Examples of suitable solvents include C4-C22 organic solvents, such as octadecene.

The amount of solvent used may be selected according to the particular reagents used and/or other reaction conditions applied. Typically, the concentration of the lead (IV) containing compound in the solvent (at the start of the reaction) may be in the range of 0.005 to 0.10 mmol/ml. Typically, the concentration of lead atoms in the solvent (at the start of the reaction) may be in the range of 0.015 to 0.30 mmol/ml. Typically, the concentration of the organic acid in the solvent (at the start of the reaction) may be in the range of 0.0075 to 10 mmol/ml, such as 0.1 to 2 mmol/ml. It is believed that the amount of solvent may affect the size of the eventual lead-chalcogenide nanocrystals formed and so the selection of the amount of solvent to be used in the method may assist in the fine tuning of their optical properties. For example, it is believed that decreasing the amount of solvent may typically result in larger nanocrystals being produced.

Suitably, the method of the present invention is conducted in an inert atmosphere. Any suitable inert atmosphere may be used, such as nitrogen or argon.

Suitably, the lead (IV) containing compound may be contacted with the organic acid for a period of time necessary to establish the preparation of the lead salt. The suitable reaction time will depend on the particular reagents and reaction conditions being used. A typical reaction time may, for example, be in the range of 10 minutes to 2 hours, such as 15 minutes to 2 hours.

Suitably, the lead salt may be contacted with the chalcogen-containing reagent for a period of time necessary to establish the preparation of the lead chalcogenide nanocrystals. The suitable reaction time will depend on the particular reagents and reaction conditions being used. A typical reaction time may, for example, be in the range of 15 minutes to 2 hours, such as 30 minutes to 2 hours.

The method of the invention may comprise:
  forming a first solution of the lead (IV) containing compound and organic acid in a first solvent;
  forming a second solution of the chalcogen-containing reagent (for example bis(trimethylsilyl)sulphide) in a second solvent;
  heating the first solution to a first temperature in the range of from 120 to 250° C. and maintaining the first solution at the first temperature for a predetermined length of time;
  reducing the temperature of the first solution to a reduced temperature in the range of from 20 to 100° C.;
  adding the second solution to the first solution at the reduced temperature to produce a reaction mixture;
  maintaining the reaction mixture at a temperature of from 20 to 300° C. for a predetermined length of time.

The method of the invention may comprise:
  forming a first solution of the lead (IV) containing compound and organic acid in a first solvent;
  forming a second solution of the chalcogen-containing reagent (for example bis(trimethylsilyl)sulphide) in a second solvent;
  heating the first solution to a first temperature in the range of from 120 to 250° C. and maintaining the first solution at the first temperature for a predetermined length of time;
  reducing the temperature of the first solution to a reduced temperature in the range of from 20 to 60° C.;
  adding the second solution to the first solution at the reduced temperature to produce a reaction mixture;
  maintaining the reaction mixture at a temperature of from 20 to 60° C. for a predetermined length of time.

The method of the invention may comprise:
forming a first solution of the lead (IV) containing compound and organic acid in a first solvent;
heating the first solution to a first temperature in the range of from 120 to 250° C. and maintaining the first solution at the first temperature for a predetermined length of time;
providing the first solution at a second temperature in the range of from 50 to 100° C.;
adding the chalcogen-containing reagent (for example thioacetamide) to the first solution at the second temperature to produce a reaction mixture;
maintaining the reaction mixture at a temperature of from 50 to 300° C. for a predetermined length of time.

The method of the invention may comprise:
forming a first solution of the lead (IV) containing compound and organic acid in a first solvent;
heating the first solution to a first temperature in the range of from 120 to 250° C. and maintaining the first solution at the first temperature for a predetermined length of time;
providing the first solution at a second temperature in the range of from 50 to 150° C.;
adding the chalcogen-containing reagent (for example thioacetamide) to the first solution at the second temperature to produce a reaction mixture;
maintaining the reaction mixture at a temperature of from 50 to 150° C. for a predetermined length of time.

The method of the invention may comprise:
forming a first solution of the lead (IV) containing compound and organic acid in a first solvent;
forming a second solution of the chalcogen-containing reagent (for example tri-n-octylphosphine selenide (TOPSe)) in presence of diphenylphosphine (DPP) in a second solvent;
heating the first solution to a first temperature in the range of from 120 to 250° C. and maintaining the first solution at the first temperature for a predetermined length of time;
reducing the temperature of the first solution to a reduced temperature in the range of from 20 to 100° C.;
adding the second solution to the first solution at the reduced temperature to produce a reaction mixture;
maintaining the reaction mixture at a temperature of from 20 to 300° C. for a predetermined length of time.

The method of the invention may comprise:
forming a first solution of the lead (IV) containing compound and organic acid in a first solvent;
forming a second solution of the chalcogen-containing reagent (for example tri-n-octylphosphine selenide (TOPSe)) in presence of diphenylphosphine (DPP) in a second solvent;
heating the first solution to a first temperature in the range of from 120 to 250° C. and maintaining the first solution at the first temperature for a predetermined length of time;
reducing the temperature of the first solution to a reduced temperature in the range of from 20 to 100° C.;
adding the second solution to the first solution at the reduced temperature to produce a reaction mixture;
maintaining the reaction mixture at a temperature of from 50 to 180° C. for a predetermined length of time.

The method of the present invention may further comprise monitoring an optical property (i.e. of the reaction mixture, such as a solution of the reactants) so as to monitor the progress of the production of the nanocrystals. The optical property may be a UV-visible-near infrared absorbance spectrum. The method may comprise the step of stopping the reaction when a value of the optical property corresponds to the desired size and/or size distribution of the lead chalcogenide nanocrystals.

The method of the invention may further comprise isolating the lead-chalcogenide nanocrystals from the reaction mixture. Any suitable method of isolating the lead-chalcogenide nanocrystals may be used.

The method of the invention may comprise quenching the reaction mixture, for example by adding a quenching solvent to the reaction mixture. Any suitable quenching solvent may be used, such as acetone, methanol, ethanol or hexane. The method of the invention may further comprise isolating the lead chalcogenide nanoparticles.

For example, the lead-chalcogenide nanocrystals may be precipitated from the reaction mixture using a suitable solvent, such as a polar solvent (for example acetone, methanol or ethanol). The isolation step may be conducted in an inert atmosphere or in air.

Examples of a method of the present invention are shown in FIG. 13 and FIG. 15. FIG. 13 and FIG. 15 show a method in which a first solution is prepared in which $Pb_3O_4$ is mixed with oleic acid in octadecene (so as to form a lead oleate salt). The first solution is mixed either with a solution of bis(trimethylsilyl)sulphide in octadecene at a temperature of from room temperature (for example 20° C.) to 60° C., or is mixed with thioacetamide (with or without solvent) at a temperature of from 50 to 300° C., or is mixed a solution of tri-n-octylphosphine selenide (TOPSe) in presence of diphenylphosphine (DPP) in octadecence at a temperature of from 50 to 300° C. so as to provide the desired nanocrystals.

An example of a method of the present invention is shown in FIG. 14. FIG. 14 shows a step 1 which is the preparation of a solution 1 (for example comprising a lead (IV) containing compound and organic acid in a first solvent, such as octadecene) and a step 2 which is the preparation of a solution 2 (for example comprising a chalcogen-containing reagent in a second solvent, such as octadecene). The method shown in FIG. 14 comprises the step 3 in which solution 2 is injected quickly into solution 1 at a pre-defined temperature (such as the suitable temperatures discussed herein), the step 4 of maintaining the temperature of the mixture resulting from step 3 at the pre-defined temperature for a period of time until a desired particle size is reached, a step 5 in which the reaction is terminated/quenched and a step 6 in which the resultant nanoparticles are purified.

When the chalcogen-containing reagent comprises bis(trimethylsilyl)sulphide, it is believed that the amount of organic acid (for example oleic acid) greatly influences the size of the nanocrystals prepared. Typically, the more organic acid introduced, the larger the size of nanocrystals were made. For example, peak absorption of the nanocrystals was observed to red shift from 652 nm to 1220 nm by simply increasing the amount of oleic acid by 27.5 times (all other reagents and conditions being equal).

When the chalcogen-containing reagent comprises bis(trimethylsilyl)sulphide, it is believed that through multi-step additions of the bis(trimethylsilyl)sulphide, peak absorption of the nanocrystals was observed to further red shift to 1304 nm from 1120 nm.

When the chalcogen-containing reagent comprises bis(trimethylsilyl)sulphide, it is believed that multi-step additions of the lead (IV) containing compound and/or of the bis(trimethylsilyl)sulphide typically produces larger nanocrystals.

When the chalcogen-containing reagent comprises bis(trimethylsilyl)sulphide, it is believed that increasing the temperature at which the bis(trimethylsilyl)sulphide is reacted with the lead salt from 40° C. to 60° C., typically provides larger nanocrystals. It was observed that the peak absorption of the nanocrystals could red shift to 986 nm from the reference 652 nm.

When the chalcogen-containing reagent comprises bis(trimethylsilyl)sulphide, it is believed that introducing acetone, alcohols or water could result in ultra-small sizes of nanocrystals. It was observed that the peak absorption of the nanocrystals was blue shifted by 24 nm by quickly adding a small amount of acetone after injection of the bis(trimethylsilyl)sulphide to the lead salt.

When the chalcogen-containing reagent comprises bis(trimethylsilyl)sulphide, it is believed that introducing cold hexane quickly after injection of the bis(trimethylsilyl) sulphide results in small nanocrystals being formed. A blue shift from 652 nm to 533 nm was observed.

When the chalcogen-containing reagent comprises bis(trimethylsilyl)sulphide, it is believed that reducing the concentration of lead oleate by increasing the amount of solvent (for example octadecene) results in the formation of smaller nanocrystals and 40 nm blue shift was observed.

When the chalcogen-containing reagent comprises bis(trimethylsilyl)sulphide, it is believed that any combinations of the above method steps may be used to produce a broad range of nanocrystals at a temperature (i.e. for the reaction of the bis(trimethylsilyl)sulphide with the lead salt) of from 20 to 60° C.

When the chalcogen-containing reagent comprises thioacetamide, the method may be simplified as it is acceptable to simply load the thioacetamide into the reaction (i.e. without first dissolving the thioacetamide into a solvent) or load the solution of thioacetamide in a solvent or a mixture of solvents.

When the chalcogen-containing reagent comprises thioacetamide, it is believed that the amount of organic acid (such as oleic acid) greatly influences the size of the nanocrystals prepared, such that the more organic acid used then the larger the size of the nanocrystals prepared.

When the chalcogen-containing reagent comprises thioacetamide, it is believed that increasing the temperature of the reaction of the thioacetamide with the lead salt (for example to a temperature of about 85° C.) greatly influences the size of the nanocrystals prepared, such that the higher the temperature used then the larger the size of the nanocrystals prepared.

When the chalcogen-containing reagent comprises thioacetamide, it is believed that reducing the concentration of the lead salt (such as lead oleate) in the solvent, i.e. by increasing the amount of solvent, may provide smaller nanocrystals.

When the chalcogen-containing reagent comprises thioacetamide, it is believed that introducing acetone, alcohols or water could result in ultra-small sizes of nanocrystals When the chalcogen-containing reagent comprises thioacetamide, it is believed that introducing cold hexane quickly after injection of thioacetamide results in small nanocrystals being formed.

When the chalcogen-containing reagent comprises thioacetamide, it is believed that any combinations of the above method steps may be used to produce a broad range of nanocrystals at a temperature (i.e. for the reaction of the thioacetamide with the lead salt) of from 50 to 300° C., suitably 50 to 150° C.

When the chalcogen-containing reagent comprises tri-n-octylphosphine selenide (TOPSe) in the presence of DPP, it is believed that the amount of organic acid (such as oleic acid) greatly influences the size of the nanocrystals prepared, such that the more organic acid which is used, the larger the size of the nanocrystals prepared.

When the chalcogen-containing reagent comprises tri-n-octylphosphine selenide (TOPSe) in the presence of DPP, it is believed that multi-step additions of TOPSe typically produces larger nanocrystals.

When the chalcogen-containing reagent comprises tri-n-octylphosphine selenide (TOPSe) in the presence of DPP, it is believed that multi-step additions of the lead (IV) containing compound and/or of TOPSe typically produces larger nanocrystals.

When the chalcogen-containing reagent comprises tri-n-octylphosphine selenide (TOPSe) in the presence of DPP, it is believed that increasing the temperature at which the TOPSe is reacted with the lead salt greatly influences the size of the nanocrystals prepared, such that the higher the temperature which is used, then the larger the size of the nanocrystals produced.

When the chalcogen-containing reagent comprises tri-n-octylphosphine selenide (TOPSe) in the presence of DPP, it is believed that introducing acetone, alcohols, water, or mixtures thereof could result in ultra-small sizes of nanocrystals, i.e., enables size reduction compared to a reaction without said solvents.

When the chalcogen-containing reagent comprises tri-n-octylphosphine selenide (TOPSe) in the presence of DPP, it is believed that introducing cold hexane quickly after injection of the solution of TOPSe results in small nanocrystals being formed.

When the chalcogen-containing reagent comprises tri-n-octylphosphine selenide (TOPSe) in the presence of DPP, it is believed that reducing the concentration of lead oleate by increasing the amount of solvent (for example octadecene) results in the formation of smaller nanocrystals, i.e., enables size reduction compared to a reaction with less solvent.

When the chalcogen-containing reagent comprises tri-n-octylphosphine selenide (TOPSe) in the presence of DPP, it is believed that any combinations of the above method steps may be used to produce a broad range of nanocrystals at a temperature (i.e. for the reaction of the TOPSe with the lead salt) of from 50 to 300° C.

The method of the present invention produces lead-chalcogenide nanocrystals. Suitably, the nanocrystals may comprise quantum dots (i.e. crystalline quantum dots).

Some specific synthesis strategies are provided below:

To make large PbS nanocrystals at 40° C. using $Pb_3O_4$, it was found that:

1) The amount of oleic acid (OA) greatly influences the size of PbS nanocrystals. The more OA introduced, the larger size of PbS nanocrystals were made. For example, peak absorption of PbS nanocrystals was observed to red shift from 652 nm to 1168 nm by increasing OA amount by 16 times.
2) Through multi-step additions of $(TMS)_2S$, peak absorption of PbS nanocrystals was observed to further red shift to 1304 nm from 1168 nm.
3) Multi-step additions of both lead and sulphur precursors also helps make large PbS quantum dots (QDs).
4) Increase temperature to 60° C., where the temperature is still low enough to remain better reaction control for injection and reaction mixing, enables making large PbS QDs. It was observed that the peak absorption of PbS nanocrystals could red shift to 1426 nm from the reference 1220 nm.
5) Introducing other sulphur precursors such as thioacetamide (TAA) or element S or tri-n-octylphosphine sulphide or tributylphosphine sulphide or alkyl substituted thiourea precursors could effectively make large PbS nanoparticles.

In addition to five methods immediately above, part and full combinations of above five synthetic strategies could effectively produce large PbS nanocrystals at low temperature (i.e., about 40° C.).

To make small PbS nanocrystals at 40° C. using $Pb_3O_4$, it was found that:
1) The amount of oleic acid (OA) greatly influences the sizes of PbS nanocrystals. The less OA, the small PbS nanocrystals were made. It was found that 652 nm peak wavelength of PbS nanocrystals was obtained when the ratio of OA to lead was lowered to 2:1.
2) Lowering temperature from 40° C. to room temperature could see blue shift by about 50 nm.
3) Introducing acetone, alcohols or water could result in ultra-small sizes of PbS nanocrystals. It was observed that the peak absorption of PbS nanocrystals was blue shifted by about 100 nm by adding a small amount of acetone after injection of sulphur precursor in lead oleate
4) Introducing cold hexane after injection of sulphur precursor resulted in small PbS nanocrystals. A blue shift from 652 nm to 533 nm was observed.
5) Reducing concentration of lead oleate by increasing the amount of ODE helps to achieve small PbS nanocrystals and 50 nm blue shift was observed.

In addition to five methods immediately above, part or full combination of above five strategies for making smaller PbS nanocrystals and the opposite ways of making larger PbS nanocrystals could form effective ways of making smaller PbS nanocrystals at low temperature (i.e., about 40° C.).

In parallel, low-cost and less toxic TAA was used to replace expensive, toxic and extremely malodour $(TMS)_2S$ precursor for making PbS nanocrystals. It was found that the threshold temperature for TAA reaction was at about 50° C. and the higher temperature applied, the larger PbS nanocrystals were made. Also, the amount of oleic acid could affect the size of PbS and it was found that the larger amount of OA applied, the larger PbS nanocrystals was achieved.

Therefore, the present invention enables PbS QDs which operate at low temperature (for example 40° C.) in the visible and NIR range using $(TMS)_2S$ and TAA reagents.

It is believed that above strategies also work for tuning particle size and absorption and emission wavelength of PbSe nanocrystals. In addition, it is believed the feed molar ratio of lead to chalcogenide (for example selenide) and the reaction time effectively control the particle size of the resulting nanocrystals. For example, the high ratio of lead to chalcogenide typically results in smaller nanocrystal size, while long reaction time leads to larger nanocrystals size.

Nanocrystals/Quantum Dots

The present invention provides one or more (preferably a plurality of, i.e., a composition) of lead chalcogenide nanocrystals obtained by the method set out above.

Suitably, the lead chalcogenide nanocrystals exhibit absorption in the visible and near infra-red ranges, for example in a range of from about 500 to 4500 nm, such as from about 500 to 2400 nm, such as from about 530 to 2400 nm, such as from about 530 to 1600 nm.

Suitably, the lead chalcogenide nanocrystals exhibit emission in the visible and near infra-red ranges, for example in a range of from about 600 to 4500 nm, such as from about 600 to 2500 nm, such as from about 630 to 2500 nm, such as from about 630 to 1700 nm.

The lead chalcogenide nanocrystal composition according to the invention comprises or consists of nanocrystals having a mean particle size in the range of 2 to 22 nm, preferably 5-20 nm, and a relative size dispersion of less than 25%. Preferably, said nanocrystals have a mean particle size in the range of 2 to 17 nm, and a relative size dispersion of less than 22%. Preferably, said nanocrystals have a mean particle size in the range of 2 to 10 nm, and a relative size dispersion of less than 20%.

Preferably, the PbS nanocrystal composition according to the invention comprises or consists of nanocrystals having a mean particle size in the range of 2 to 10 nm, and a relative size dispersion of less than 25%, preferably less than 20%.

The PbSe nanocrystal composition according to the invention comprises or consists of nanocrystals having a mean particle size in the range of 2 to 17 nm, and a relative size dispersion of less than 25%, preferably less than 22%.

The lead chalcogenide nanocrystal compositions according to the eighth aspect of the invention preferably contain lead chalcogenide nanocrystals having a mean particle size in the range of 2 to 20 nm, preferably 2 to 17 nm, preferably 2 to 10 nm.

The lead chalcogenide nanocrystal compositions according to the eighth aspect of the invention preferably contain greater than 0.001% by weight of lead chalcogenide nanocrystals, preferably greater than 0.01% by weight, preferably greater than 0.1% by weight, preferably greater than 1% by weight, preferably greater than 5% by weight.

In some applications, lead chalcogenide nanocrystal compositions according to the eighth aspect of the invention preferably contain greater than 5% by weight of lead chalcogenide nanocrystals, preferably greater than 30% by weight, preferably greater than 75% by weight, preferably greater than 90% by weight, preferably greater than 95% by weight.

In one embodiment, the lead chalcogenide nanocrystal compositions according to the eighth aspect of the invention consist of lead chalcogenide nanocrystals.

The remainder of the composition, which is not lead chalcogenide nanocrystals, may be a carrier material, such as a solvent, additives, inorganic ligands, organic ligands or a reaction by-product.

The present invention also provides a composition of lead chalcogenide nanocrystals directly obtained by the method set out above.

The present invention also provides a composition of lead chalcogenide nanocrystals obtainable by the method set out above.

The composition of lead chalcogenide nanocrystals may comprise one or more quantum dots (i.e. crystalline quantum dots). The present invention provides a composition of lead chalcogenide quantum dots obtained by the method set out above.

The present invention also provides a composition of lead chalcogenide quantum dots directly obtained by the method set out above.

The present invention also provides a composition of lead chalcogenide quantum dots obtainable by the method set out above.

The lead chalcogenide nanocrystals (for example lead chalcogenide quantum dots) and compositions, films, systems or components containing said lead chalcogenide nanocrystals, may be used for any suitable purpose. For example, lead chalcogenide nanocrystals and compositions thereon may be used to provide for, or be used in photodetector, sensor, solar cell, bio-imaging or bio-sensing composition, photovoltaic system, display, battery, laser, photocatalyst, spectrometer, injectable composition, field-effect transistor, light-emitting diode, photonic or optical switching device or metamaterial, thermoelectric (cooling) and energy (high temperature power) generation applications, fiber amplifier, laser, optical gain media, optical fiber communication, highspeed communications, telecommunication, infrared LEDs and lasers, electroluminescent device.

The lead chalcogenide nanocrystal compositions (for example lead chalcogenide quantum dots) may also be used for IR sensing and photodetectors. For example, the lead chalcogenide nanocrystals (for example lead chalcogenide quantum dots) may be used as light absorbers in 3D camera sensors and 3D Time of flight camera sensors in mobile and consumer, automotive, medical, industrial, Defence and aerospace applications.

The lead chalcogenide nanocrystal compositions (for example lead chalcogenide quantum dots) may also be used in bio-imaging and bio-sensing applications. For example, the lead chalcogenide nanocrystals (for example lead chalcogenide quantum dots) may be used as bio-labels or bio-tags in in vitro and ex vivo applications.

The lead chalcogenide nanocrystal compositions (for example lead chalcogenide quantum dots) may also be used in wired, high speed communication devices, night vision devices and solar energy conversion.

The present invention provides a film comprising the lead chalcogenide nanocrystal compositions of the present invention.

The present invention provides a system or component, such as a photodetector, sensor, solar cell, bio-imaging or bio-sensing composition, photovoltaic system, display, battery, laser, photocatalyst, spectrometer, injectable composition, field-effect transistor, light-emitting diode, photonic or optical switching device or metamaterial, thermoelectric (cooling) and energy (high temperature power) generation applications comprising the lead chalcogenide nanocrystal compositions of the present invention.

The present invention provides a bio-label or bio-tag, biological imaging and labelling (in vitro and in vivo), comprising the lead chalcogenide nanocrystals of the present invention.

The processes of the present invention lead to excellent full width at half maximum (FWHM) values for the nanocrystals of the present invention. FWHM refers to the width of an optical signal at half its maximum intensity. This measure gives the bandwidth of a light source operating at 50% capacity.

The emissive properties of the nanocrystals of the present invention are both chemistry and size dependent. They usually exhibit an emissive function in the shape of a Gaussian curve. Lower intensities may result in broader spectral bandwidths and less pure colour representation onscreen. To determine the FWHM, the difference must be calculated between the low and high wavelength points at half the maximum spectral intensity. The narrower FWHM of the invention offer higher signal to noise ratio and allow the tuning of absorption wavelength more precisely. Essentially, narrower bandwidths translate to purer colours with higher levels of efficiency.

For example, the processes of the present invention can produce nanocrystals having a maximum absorption wavelength ($\lambda_{max}$) of 500 to 1000 nm, preferably 600 to 975 nm, preferably 700 to 775 nm and emission wavelength or photoluminescence (PL) of 600 to 1200 nm, preferably 700 to 1100 nm, preferably 800 to 950 nm. The compositions according to the eighth aspect of the invention can be produced having an absorption FWHM of less than 130 nm, preferably less than 120 nm, for example about 110 nm and an emission FWHM of less than 130 nm, preferably less than 120 nm, for example about 110 nm. These properties can be provided by nanocrystal compositions having relative size dispersions less than 20%.

The nanocrystals of the compositions according to the eighth aspect of the invention have a good relative size dispersion as a consequence of the processes used in the present invention. The relative size dispersion is a measure of the variance of the nanocrystal particle size. It is determined by measuring the particle sizes of a particular batch of nanoparticles and determining the variance to the mean size. This can be expressed as a particular average size, x, plus or minus the range of particle size. For example, the present invention can produce nanocrystals having a maximum absorption wavelength of 950 nm and emission peak at 1060±5 nm. These particles have a size of 3.10±0.52 (as determined by transmission electron microscope (TEM)). This produces a relative size dispersion of 16.8% ((0.52/3.10)×100).

In general, the processes of the present invention enable the production of nanoparticle compositions according to the eighth aspect of the invention having a relative size dispersion (determined by TEM) of less than 25%, preferably less than 22%, preferably less than 20%

In a preferred embodiment of the invention, the nanocrystal compositions according to the eighth aspect of the invention have a molar ratio of lead atoms to chalcogen atoms in the range of from 1.2:1 to 4:1, preferably 1.6:1 to 3:1. This preferred range can be achieved for each of the PbS, PbSe and PbTe nanocrystals.

These ratios of lead atoms to chalcogen atoms are correlated to the low relative size distributions exhibited by the nanocrystals of the invention. Generally, the nanocrystal compositions according to the eighth aspect of the invention, having a molar ratio of lead atoms to chalcogen atoms in the range of from 1.2:1 to 4:1, have a relative size dispersion of less than 20%, for example, less than 18%, such as between 10 and 17%.

Generally, higher Pb to S ratio in lead sulphur nanocrystal composition correlates to large nanocrystal size and longer $\lambda_{max}$ of PbS dots. Generally, lower Pb to Se ratios (or increase in Se molar ratio) in lead selenium nanocrystal composition correlates to larger nanocrystal size and longer $\lambda_{max}$.

The molar ratio of lead atoms to chalcogen atoms is measured by inductively coupled plasma optical emission spectrometry (ICP-OES).

Generally, the PbS nanocrystal compositions according to the eighth aspect of the invention exhibit a proportional correlation between maximum absorption wavelength ($\lambda_{max}$) and their average particle size, i.e., larger dots exhibit longer $\lambda_{max}$. A similar trend in the nanoparticle size vs $\lambda_{max}$ correlation is seen for the PbSe nanocrystals. However, PbSe nanocrystals are generally smaller than PbS at the same $\lambda_{max}$. TEM images of PbS ($\lambda_{max}$=1314 nm) and PbSe ($\lambda_{max}$=2046 nm) and their histogram of particle measurements are shown in FIGS. 8a and 8b and 20a and 20b respectively.

The preferred features of the fourth to seventh aspects are as defined in relation to the first, second and third aspects.

BRIEF DESCRIPTION OF DRAWINGS

For a better understanding of the invention, and to show how exemplary embodiments of the same may be carried into effect, reference will be made, by way of example only, to the accompanying diagrammatic Figures, in which.

EXAMPLES

Several examples and comparative examples are described hereunder illustrating the methods according to the present disclosure.

Whereas particular examples of this invention have been described below for purposes of illustration, it will be evident to those skilled in the art that numerous variations of the details of the present invention may be made without departing from the invention as defined in the appended claims.

Unless otherwise indicated, all parts and all percentages in the following examples, as well as throughout the specification, are parts by weight or percentages by weight respectively.

Absorption spectra were obtained on a JASCO V-770 UV-visible/NIR spectrometer (which can provide measurements in the 400 to 3200 nm wavelength range).

Example 1: Synthesis of Lead Sulphide (PbS) Nanocrystals Using Pb$_3$O$_4$ and (TMS)$_2$S 0.19 g Pb$_3$O$_4$, 0.6 ml oleic acid and 7 ml octadecene (ODE) were loaded in a 3-necked flask, vacuumed and held under a N$_2$ atmosphere for 30 minutes at 180° C. to produce lead oleate solution. After clear lead oleate solution formed, the temperature was reduced to 40° C. 45 μl bis(trimethylsilyl)sulphide ((TMS)$_2$S) in 4 ml of ODE was swiftly injected. The solution changed from light yellow to light brown then dark brown in the next 5 minutes, suggestive of controllable nucleation. The reaction was maintained at 40° C. for 60 minutes (monitored by UV-Vis-NIR spectroscopy), then slowly cooled down to room temperature. Then 20 ml of distilled acetone was added into the reaction mixture. PbS nanocrystals were precipitated through centrifugation, redispersed in toluene, and precipitated again through a combination of acetone and centrifugation. Finally, the nanocrystals were dispersed in toluene. The purification process was carried out in air.

The PbS nanocrystals prepared in Example 1 were characterised by powder XRD and EDX measurements.

XRD samples were prepared by dropcasting the particles from a toluene solution onto the end of a microscope slide until a relatively thick opaque film was formed. This film was then analysed using a Panalytical X'Pert PRO MPD instrument.

EDX samples were prepared by dropcasting the particles from a toluene solution onto SEM specimen stubs covered with a carbon-based adhesive tab. The toluene was allowed to evaporate prior to analysis. Samples were analysed on a Philips/FEI XL30 ESEM equipped with an Oxford Instruments Energy 250 energy dispersive spectrometer system.

Figure 1:
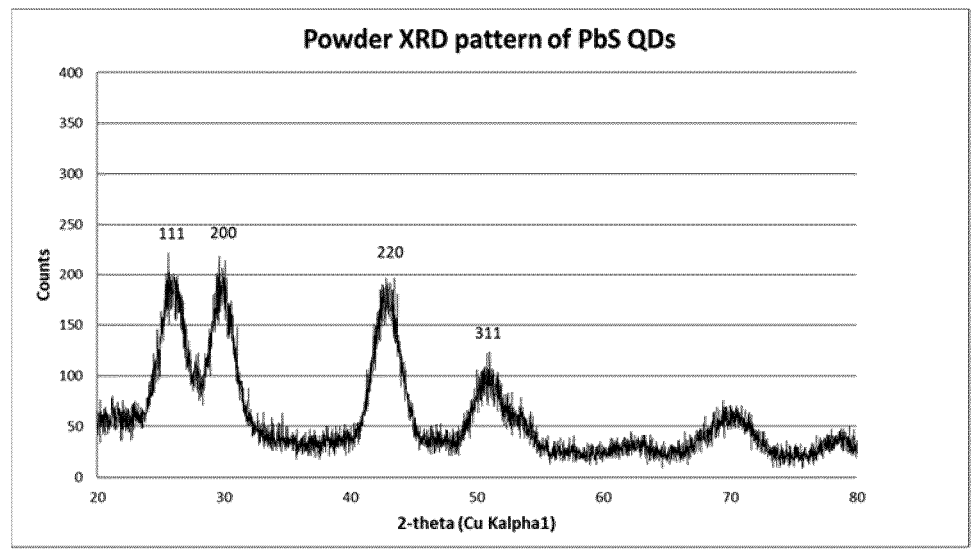
FIG. 1 shows the powder XRD pattern for the PbS nanocrystals prepared according to Example 1.

FIG. 1 shows the powder XRD pattern for the PbS nanocrystals prepared according to Example 1. The XRD pattern shown in FIG. 1 confirms that Example 1 produced PbS nanocrystals with a rock-salt structure.

The EDX measurements were as shown in Table 1 and confirmed that the nanocrystals prepared contain lead and sulphur.

TABLE 1

| Element | Weight % | Atomic % |
|---------|----------|----------|
| S K     | 8.48     | 37.46    |
| Pb M    | 91.52    | 62.54    |
| Totals  | 100.00   |          |

Figure 2:
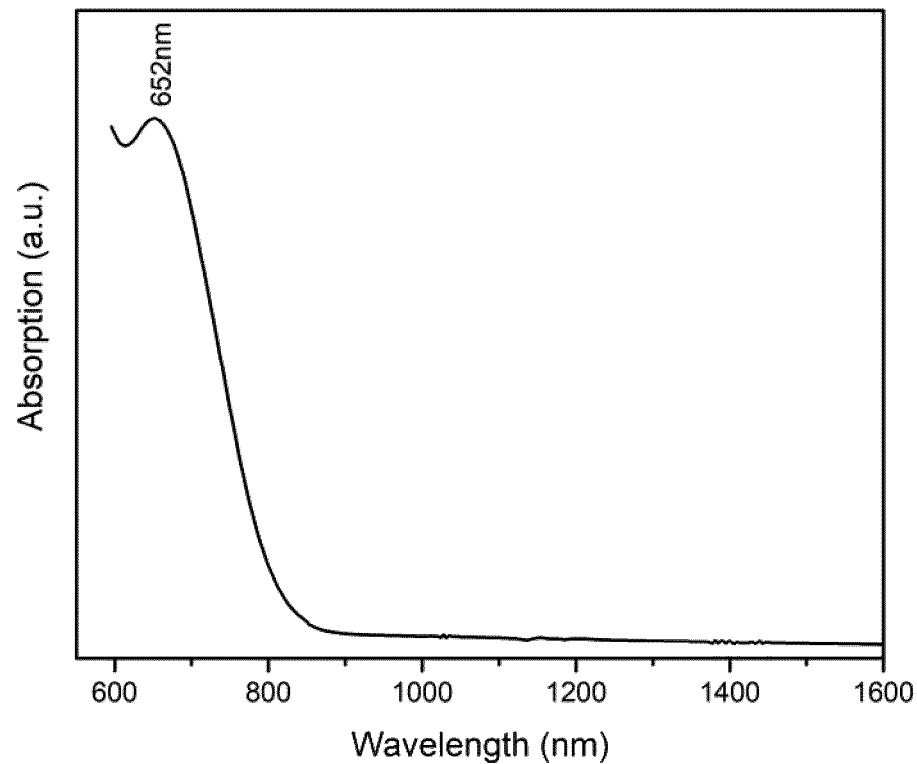
FIG. 2 shows the absorption spectrum of the PbS nanocrystals prepared in Example 1 in toluene.

The absorption spectra of the PbS nanocrystals prepared in Example 1 in toluene was obtained and the results are shown in FIG. 2.

Example 2: Synthesis of PbS Nanocrystals Using Pb₃O₄ and (TMS)₂S with Different Amounts of Oleic Acid The synthesis outlined above in Example 1 was repeated using an amount of oleic acid of 0.6 ml and using an amount of 14.4 ml.

Figure 3:
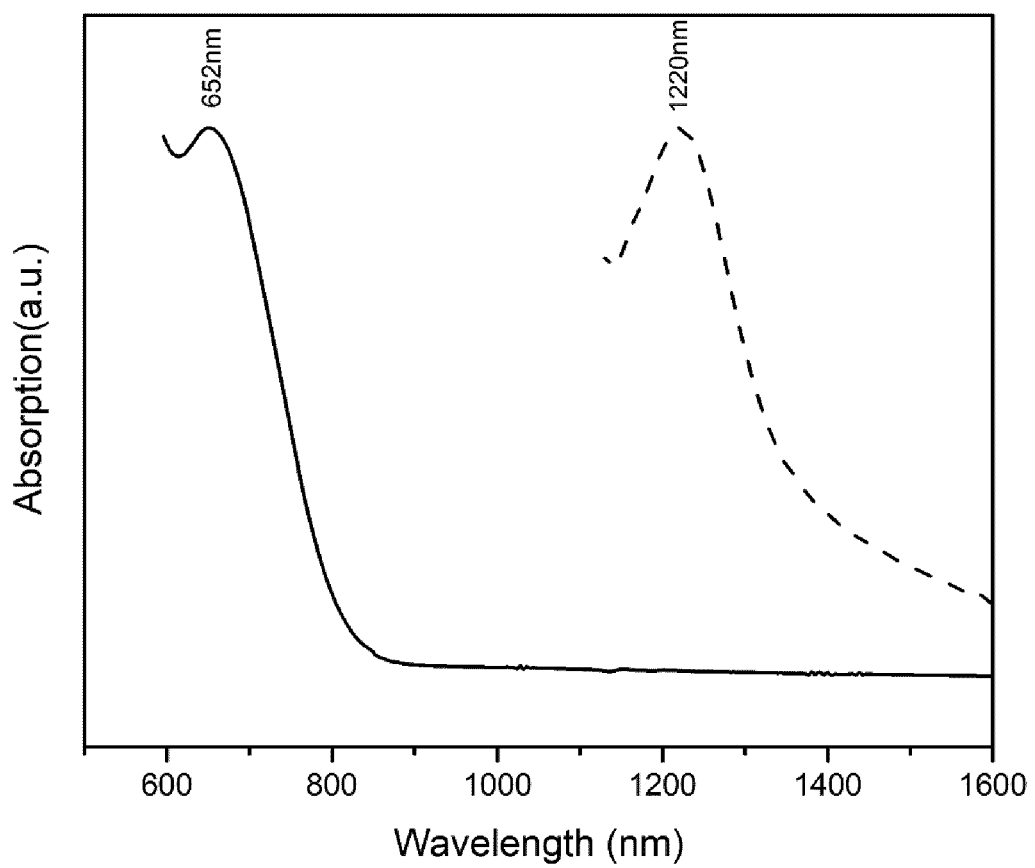
FIG. 3 shows the absorption spectra for the PbS nanocrystals obtained with different amounts of oleic acid in Example 2.

The absorption spectra for the nanocrystals obtained are shown in FIG. 3 (in which the solid line corresponds to oleic acid 0.6 ml; and the dashed line corresponds to oleic acid 14.4 ml), which shows that different amounts of oleic acid provided different sized crystals.

FIG. 3 shows that larger PbS nanocrystals were obtained when the amount of oleic acid used was 14.4 ml compared to 0.6 ml.

Example 3: Synthesis of PbS Nanocrystals Using Pb₃O₄ and (TMS)₂S at 60° C.

The synthesis outlined above in Example 1 was repeated except that the temperature for the reaction of the lead salt with the bis(trimethylsilyl)sulphide ((TMS)₂S) was changed from 40° C. to 60° C.

Figure 4:
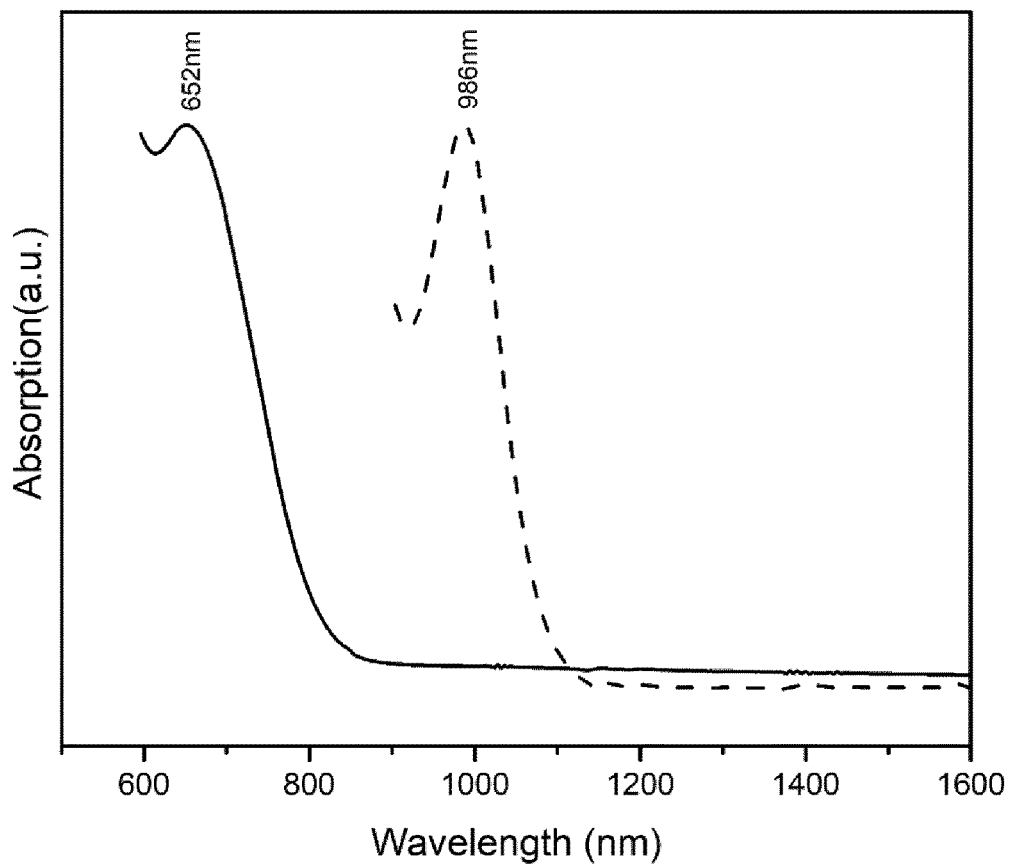
FIG. 4 shows the absorption spectra for the PbS nanocrystals obtained at 40° C. or 60° C. in Example 3.

The absorption spectra for the nanocrystals obtained at 40° C. and 60° C. are shown in FIG. 4 (in which the solid line corresponds to the reaction at 40° C.; and the dashed line corresponds to the reaction at 60° C.), which shows that different temperatures provided different sized crystals.

FIG. 4 shows that larger PbS nanocrystals were obtained when the temperature for the reaction of the lead salt with the chalcogen-containing reagent was increased.

Example 4: Synthesis of PbS Nanocrystals Using Pb₃O₄ and (TMS)₂S with Multi-Step (TMS)₂S Additions 0.19 g Pb₃O₄, 9.6 ml oleic acid and 7 ml octadecene (ODE) were loaded in a 3-necked flask, vacuumed and held under a N₂ atmosphere for 30 minutes at 180° C. to produce lead oleate solution. After clear lead oleate solution formed, the temperature was reduced to 40° C. 90 µl bis(trimethylsilyl)sulphide ((TMS)₂S) in 4 ml of ODE was swiftly injected. The reaction was maintained at 40° C. for 60 minutes, then slowly cooled down to room temperature. Then 20 ml of distilled acetone was added into the reaction mixture. PbS nanocrystals were precipitated through centrifugation, re-dispersed in toluene, and precipitated again through a combination of acetone and centrifugation. Finally, the nanocrystals were dispersed in toluene. The purification process was carried out in air.

The above method was repeated except that the bis (trimethylsilyl)sulphide (TMS) solution in ODE was divided into two equal portions and each portion added to the reaction mixture separately with a 15 minutes interval between each injection. 30 minutes after the last injection the reaction was completed.

Figure 5:
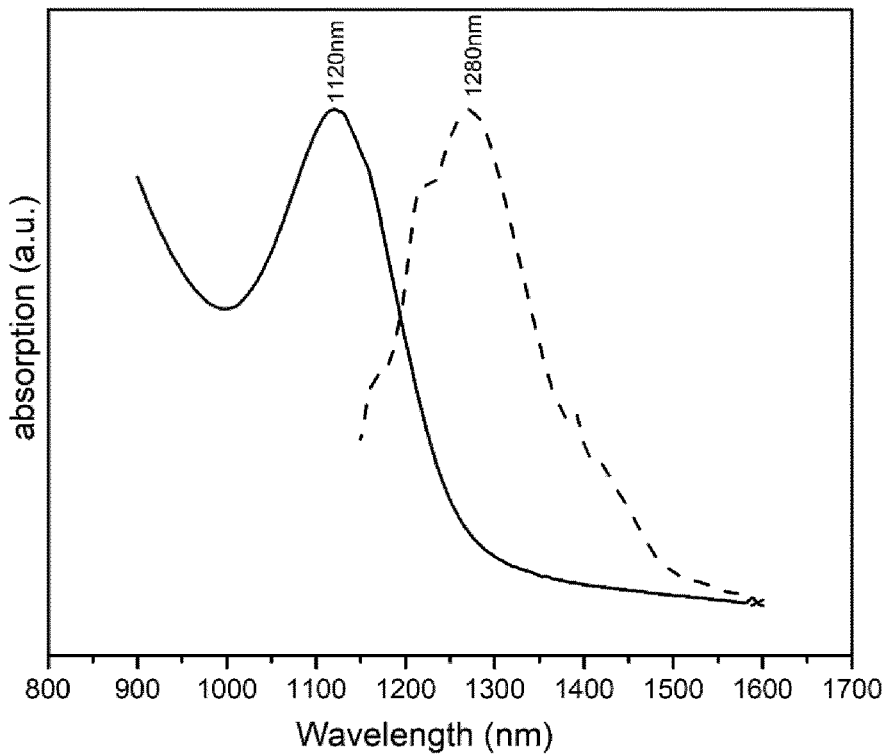
FIG. 5 shows the absorption spectra for the PbS nanocrystals obtained with a single or multiple addition of (TMS)$_2$S in Example 4.

The absorption spectra for the nanocrystals obtained with a single or multiple addition of (TMS)₂S are shown in FIG. 5 (in which the solid line corresponds to the reaction with a single addition of (TMS)₂S; and the dashed line corresponds to the reaction with two additions of (TMS)₂S), which shows that different modes of addition of the (TMS)₂S provided different sized crystals.

FIG. 5 shows that larger PbS nanocrystals were obtained when the (TMS)₂S was added by two additions compared to by a single addition.

Example 5: Synthesis of PbS Nanocrystals Using Pb₃O₄ and (TMS)₂S with Different Amounts of ODE 0.19 g Pb₃O₄, 9.6 ml oleic acid and 7 ml octadecene (ODE) were loaded in a 3-necked flask, vacuumed and held under a N₂ atmosphere for 30 minutes at 180° C. to produce lead oleate solution. After clear lead oleate solution formed, the temperature was reduced to 40° C. 45 µl bis(trimethylsilyl)sulphide ((TMS)₂S) in 4 ml of ODE was swiftly injected. The reaction was maintained at 40° C. for 60 minutes, then slowly cooled down to room temperature. Then 20 ml of distilled acetone was added into the reaction mixture. PbS nanocrystals were precipitated through centrifugation, re-dispersed in toluene, and precipitated again through a combination of acetone and centrifugation. Finally, the nanocrystals were dispersed in toluene. The purification process was carried out in air.

The above method was repeated except that the amount of ODE used to dilute the Pb₃O₄ and oleic acid before the addition of (TMS)₂S into the lead oleate solution was changed from 7 ml to 21 ml.

Figure 6:
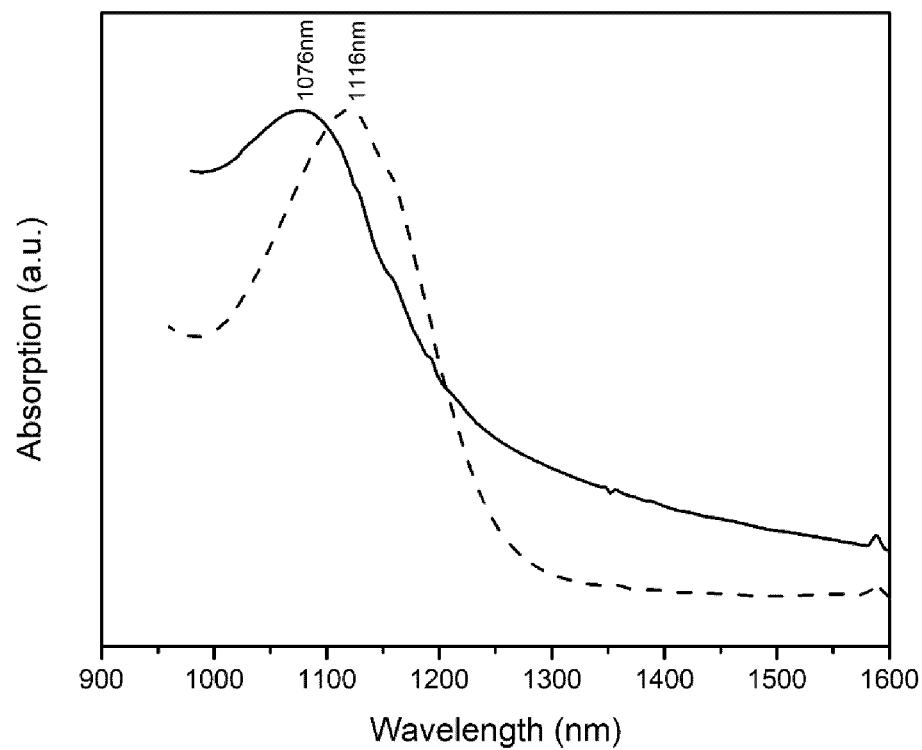
FIG. 6 shows the absorption spectra for the PbS nanocrystals obtained with different amounts of ODE in Example 5.

The absorption spectra for the nanocrystals obtained with different amounts of ODE are shown in FIG. 6 (in which the solid line corresponds to the reaction using 21 ml of ODE; and the dashed line corresponds to the reaction using 7 ml of ODE), which shows that different amounts of ODE provided different sized crystals.

FIG. 6 shows that smaller PbS nanocrystals were obtained when the amount of ODE used was increased.

Example 6: Synthesis of PbS Nanocrystals Using Pb₃O₄ and Thioacetamide (TAA)

The synthesis outlined above in Example 1 was repeated except that the (TMS)₂S was replaced by the same molar amount of thioacetamide (TAA). The latter can be added to the lead oleate as a powder or it can be dissolved in a solvent, such as Acetone, DMF or THF before injection. The reaction mixture is then heated to 50° C. and maintained at that temperature for 1 hour or to 90° C. and maintained at that temperature for 20 minutes The absorption spectra for the nanocrystals obtained using TAA and (TMS)₂S are shown in FIG. 7 (in which the solid line corresponds to the reaction using (TMS)₂S; and the dashed line corresponds to the reaction using TAA), which shows that the different reagents provided different sized crystals.

Figure 7:
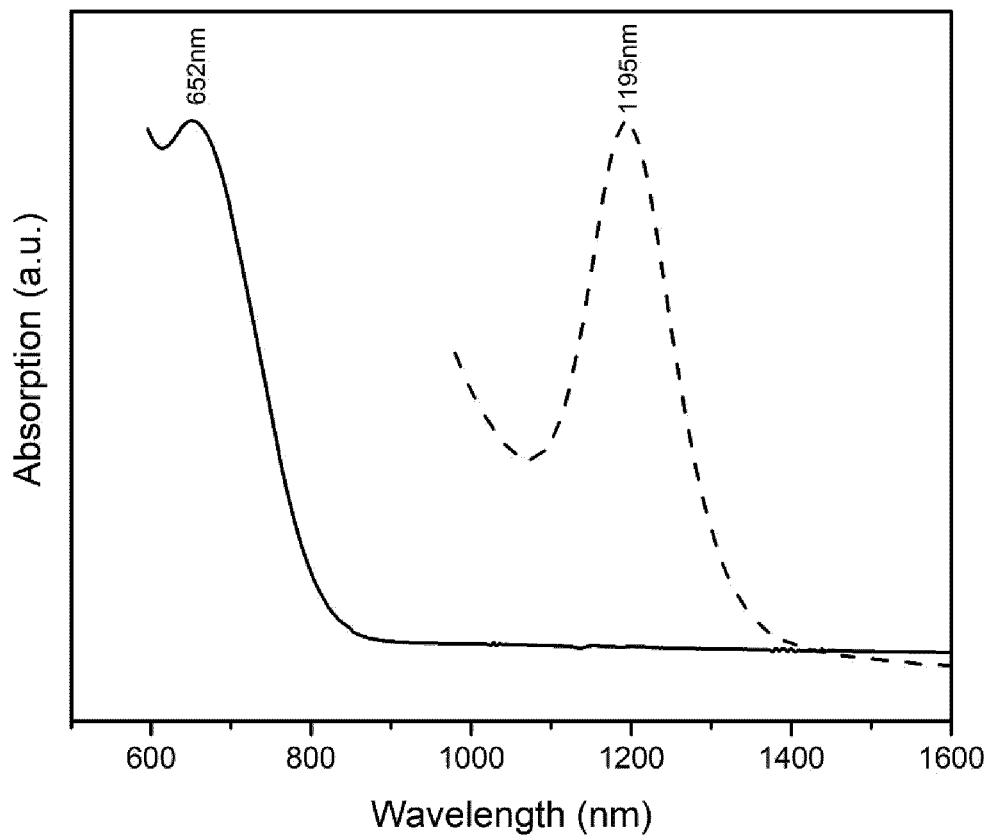
FIG. 7 shows the absorption spectra for the PbS nanocrystals obtained using TAA and (TMS)$_2$S in Example 6.

FIG. 7 shows that larger PbS nanocrystals were obtained when TAA was used instead of (TMS)₂S.

Figure 8A:
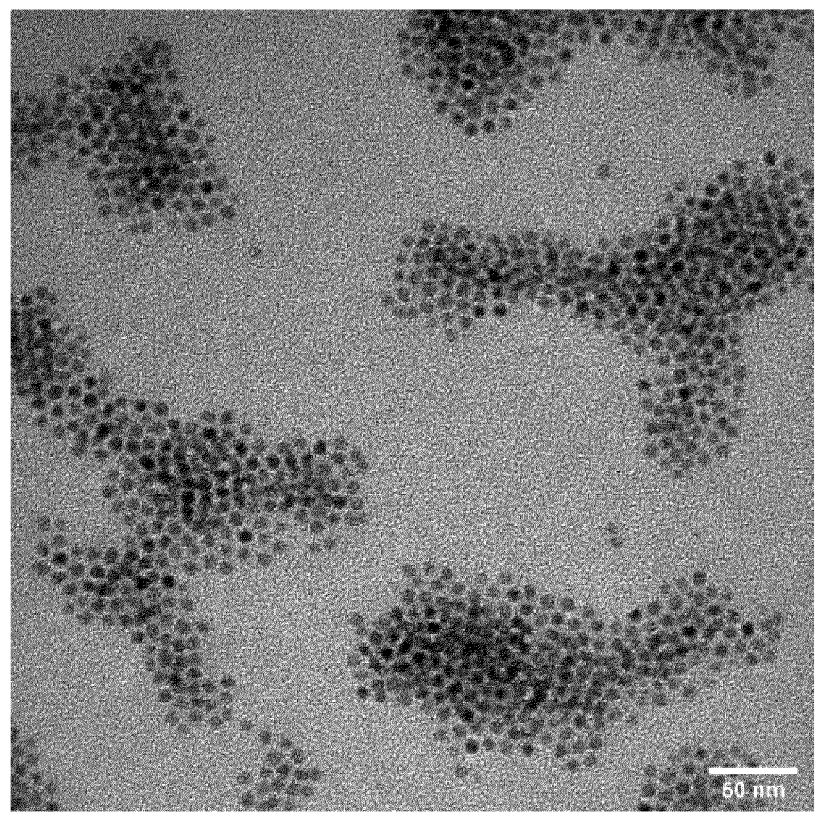
FIGS. 8a and 8b shows the TEM image of PbS nanocrystals ($\lambda_{max}$=1314 nm) and the histogram of particle measurements by TEM in Example 6.
Figure 8B:
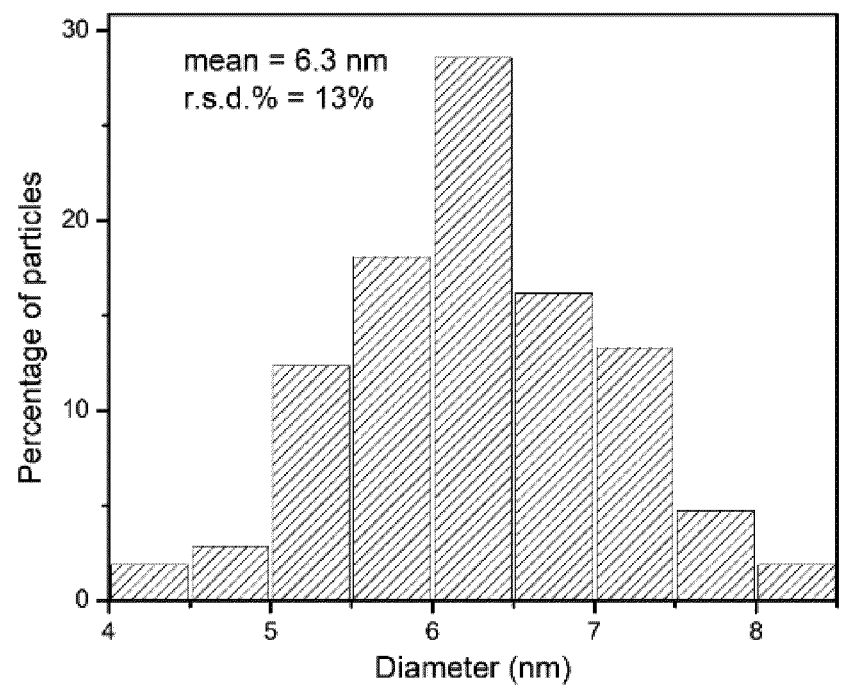

FIGS. 8a and 8b shows TEM image of PbS nanocrystals and the histogram of particle measurements by TEM. The PbS nanocrystals with maximum absorption of 1314 nm were obtained when TAA was used instead of (TMS)₂S.

Table 2 shows maximum absorption wavelength, size and composition of PbS nanocrystals obtained when TAA was used instead of (TMS)₂S shown as below. Increasing Pb to S ratio leads to increase in the maximum absorption wavelength of PbS dots;

TABLE 2

| Maximum absorption wavelength $\lambda_{max}$ (nm) | Size by TEM (nm) | Pb/S molar ratio by ICP-OES |
|---|---|---|
| 950 | 3.10 ± 0.52 | 1.69:1 |
| 1314 | 6.28 ± 0.82 | 1.93:1 |
| 1540 | 8.32 ± 1.41 | 1.97:1 |

The absorption FWHM for these nanocrystals is about 100 nm. For example, the FWHM for the nanocrystals exhibiting a maximum absorption of 950 nm is 105 nm.

Example 7: Synthesis of PbS Nanocrystals Using $Pb_3O_4$ and $(TMS)_2S$ Promoted by Addition of Acetone During Reaction The synthesis outlined above in Example 1 was repeated except that 5 ml of acetone was quickly injected into the solution 10 seconds after the $(TMS)_2S$ solution in ODE was added to the lead oleate solution.

Figure 9:
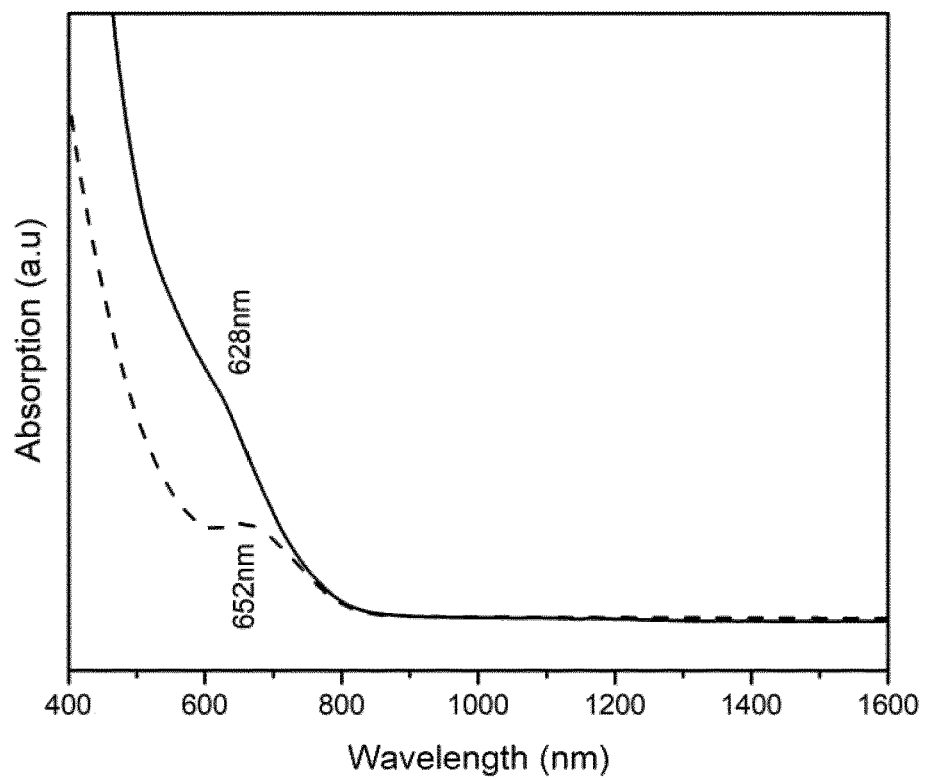
FIG. 9 shows the absorption spectra for the PbS nanocrystals obtained with and without the addition of acetone in Example 7.

The absorption spectra for the nanocrystals obtained with and without the addition of acetone are shown in FIG. 9 (in which the solid line corresponds to the reaction with the addition of acetone; and the dashed line corresponds to the reaction without addition of acetone, i.e. according to Example 1), which shows that the different reagents provided different sized crystals.

FIG. 9 shows that smaller PbS nanocrystals were obtained when acetone was added compared to Example 1.

Example 8: Synthesis of PbS Nanocrystals Using $Pb_3O_4$ and $(TMS)_2S$, Quenched by Cold Hexane During Reaction The synthesis outlined above in Example 1 was repeated, except that cold hexane was quickly injected into the solution 1.5 minutes after the $(TMS)_2S$ in ODE solution was added to the lead oleate solution.

Figure 10:
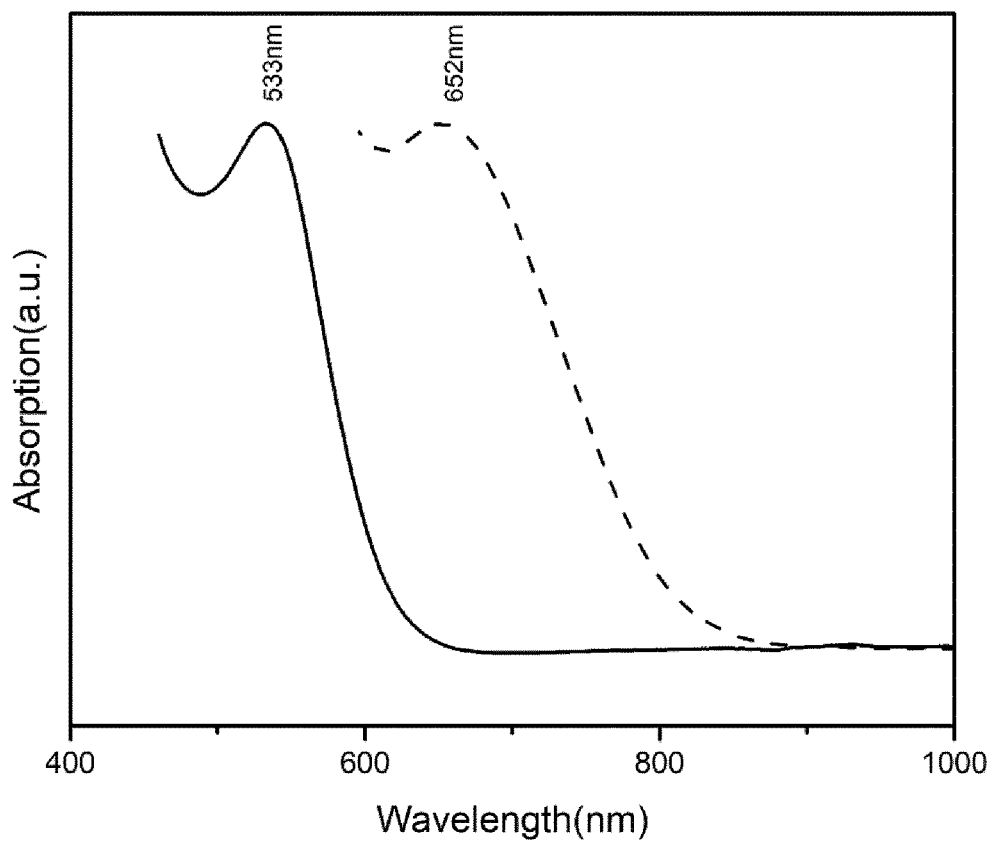
FIG. 10 shows the absorption spectra for the PbS nanocrystals obtained with and without the addition of hexane in Example 8.

The absorption spectra for the nanocrystals obtained with and without the addition of hexane are shown in FIG. 10 (in which the solid line corresponds to the reaction with the addition of hexane; and the dashed line corresponds to the reaction without addition of hexane, i.e. according to Example 1), which shows that the different reagents provided different sized crystals.

FIG. 10 shows that smaller PbS nanocrystals were obtained when hexane was added compared to Example 1.

Example 9: Synthesis of PbS Nanocrystals Using $Pb_3O_4$ and Thioacetamide (TAA)

0.35 g $Pb_3O_4$, 1 ml oleic acid and 5 ml octadecene (ODE) were loaded in a 3-necked flask, vacuumed and held under a $N_2$ atmosphere for 30 minutes at 180° C. to produce lead oleate solution. After clear lead oleate solution formed, the temperature was reduced to room temperature. 40 mg TAA was directly loaded into the flask and the reaction mixture was heated up to 50° C. and maintained at this temperature for 60 minutes. The reaction mixture was then slowly cooled down to room temperature. Then 20 ml of distilled acetone was added into the reaction mixture. PbS nanocrystals were precipitated through centrifugation, re-dispersed in toluene, and precipitated again through a combination of acetone and centrifugation. Finally, the nanocrystals were dispersed in toluene. The purification process was carried out in air.

The above method was then repeated, except that the amounts of oleic acid and the temperatures of the reaction of the lead oleate with the TAA were as follows:

| Amount of oleic acid | Temperature (lead oleate + TAA) |
| --- | --- |
| 1.4 ml | 50° C. |
| 1.4 ml | 70° C. |
| 1.4 ml | 85° C. |

Figure 11:
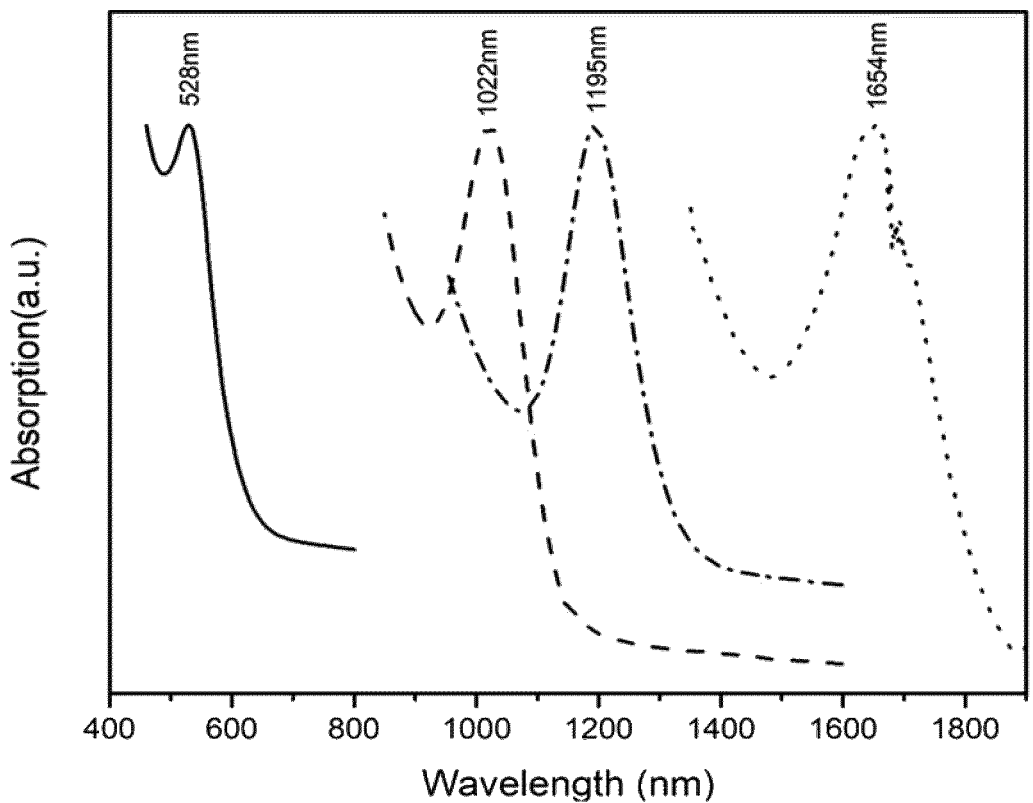
FIG. 11 shows the absorption spectra for the PbS nanocrystals obtained using different amounts of oleic acid and different reaction temperatures in Example 9.

The wide absorption spectra for the PbS nanocrystals obtained in Example 9 are shown in FIG. 11, in which the spectra from left to right corresponds to the reaction with 1 ml oleic acid at 50° C.; 1.4 ml oleic acid at 50° C.; 1.4 ml oleic acid at 70° C. and 1.4 ml oleic acid at 85° C. The spectra show that the different reaction conditions and different amounts of oleic acid provided different sized PbS nanocrystals.

Example 10: Comparison of PbS Nanocrystals Solution and Drop Casting Thin Film The synthesis outlined above in Example 1 was repeated. Thin film samples were prepared by drop casting the particles from a toluene solution onto a glass slide. The toluene was allowed to evaporate prior to analysis.

Figure 12:
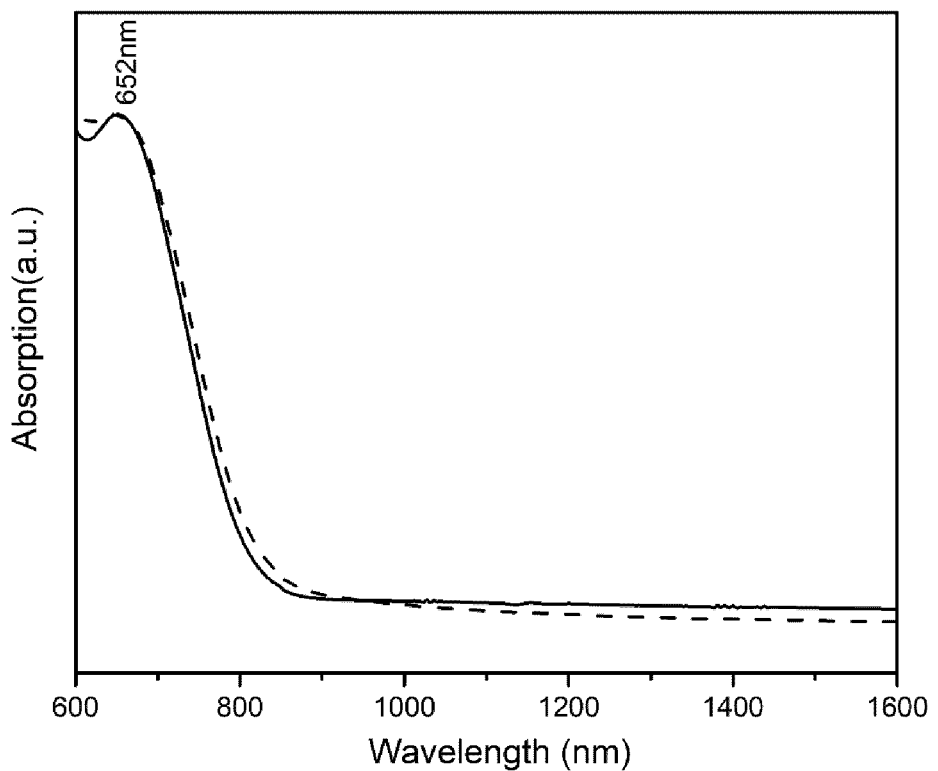
FIG. 12 shows the absorption spectra for the solution PbS nanocrystals and thin film sample as prepared in Example 10.
Figure 13:
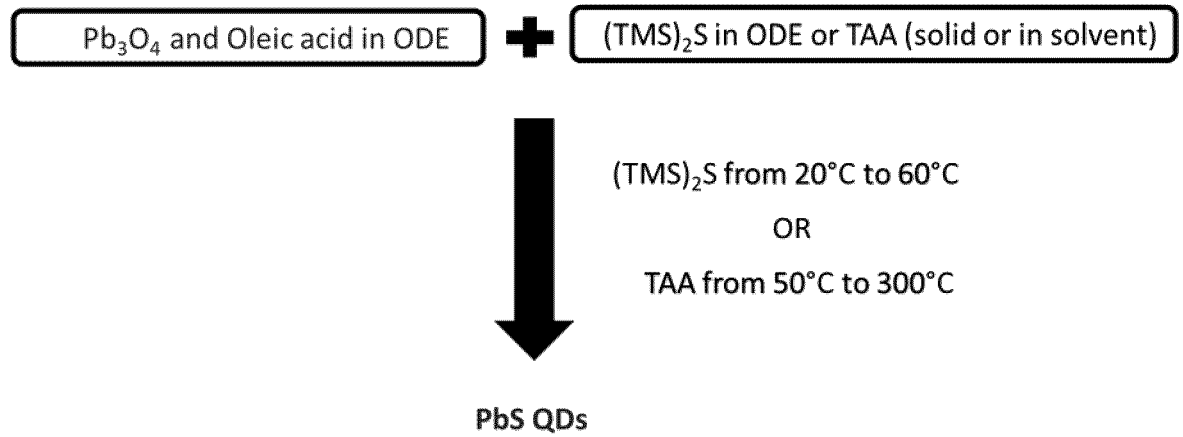
FIG. 13 shows an example of a particular method of the present invention.
Figure 14:
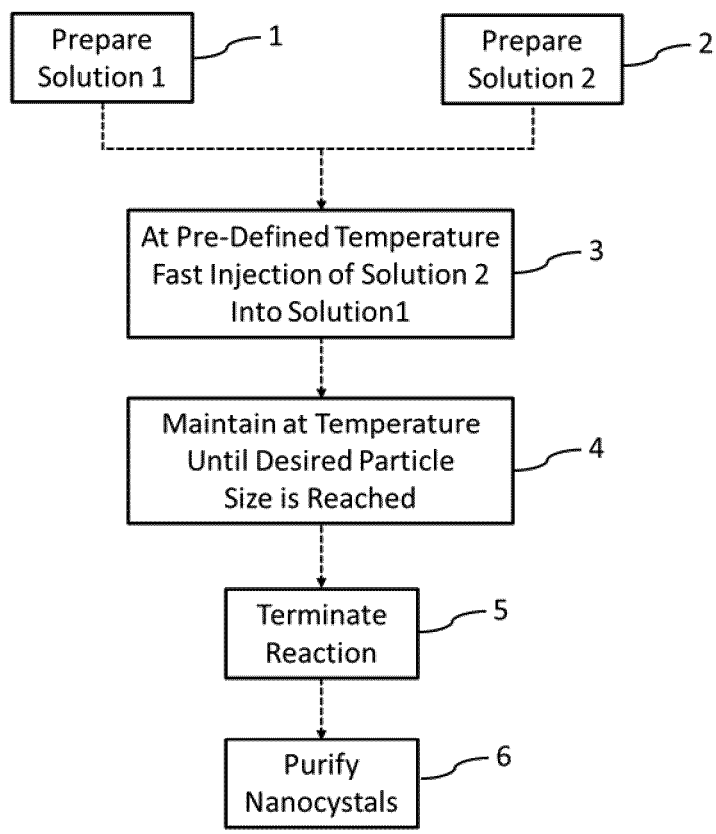
FIG. 14 shows an example of a particular method of the present invention.

The solution and thin film absorption spectra for the PbS nanocrystals are shown in FIG. 12 (in which the solid line corresponds to the solution nanocrystals; and the dashed line corresponds to the thin film sample). The absorption peaks of the both solution and thin film are very similar and well overlapped indicating there was no change on their electronic states and no self-assembly taken place after drop casting.

Example 11: Synthesis of Lead Selenide (PbSe) Nanocrystals Using $Pb_3O_4$ and TOPSe 1.5 g Pb oleate (with Pb and OA molar ratio of 1:4) and 3.9 ml octadecene (ODE) were loaded into a three-neck round bottom flask, then degassed via three cycles of vacuum/nitrogen and held under a $N_2$ atmosphere for 30 minutes at 80° C. 3.6 g TOPSe (with TOP and Se molar ratio of 2:1) was rapidly injected. After temperature of the reaction mixture reached back to 80° C., 0.06 ml DPP was injected quickly. Colour of the reaction mixture changed immediately from light brown to dark brown after DPP addition, suggesting that nucleation of PbSe nanocrystals occurred. The occurrence of nucleation is a vital initial step in the formation of PbSe nanocrystals and allows their further growth to desired size. The reaction solution was then quickly heated from 80° C. to 150° C., aliquots were taken at different temperature, quickly cooled down to room temperature (20° C.) and kept under $N_2$ prior to analysis. To purify the PbSe nanocrystals, the aliquot samples and the final reaction mixture were diluted with hexane (volume ratio of 1:1) then acetone was added (volume ratio of hexane/acetone was 1:3). The PbSe nanocrystals were precipitated through centrifugation, re-dispersed in hexane, and precipitated again through a combination of acetone and centrifugation. The purification process was carried out in air.

The PbSe nanocrystals prepared in the Example 11 were characterised using UV-Vis-NIR spectroscopy, XRD, TEM and ICP-OES.

For absorbance, the PbSe nanocrystals were dispersed either in tetrachloroethylene or hexane and their absorbance was monitored using a Jasco V-770 UV-VIS/NIR spectrometer.

XRD samples were prepared by drop casting the PbSe nanoparticle dispersions in hexane onto a microscope slide until a relatively thick opaque film was formed. This film was then analysed using a Bruker D2 Phaser instrument.

TEM samples were prepared by drop casting the PbSe nanoparticle dispersions in hexane onto a copper grid. The solvent was allowed to evaporate prior to analysis. Samples were analysed on a FEI Titan G2 80-200 kV (S-)TEM ChemiSTEM instrument.

Figure 15:
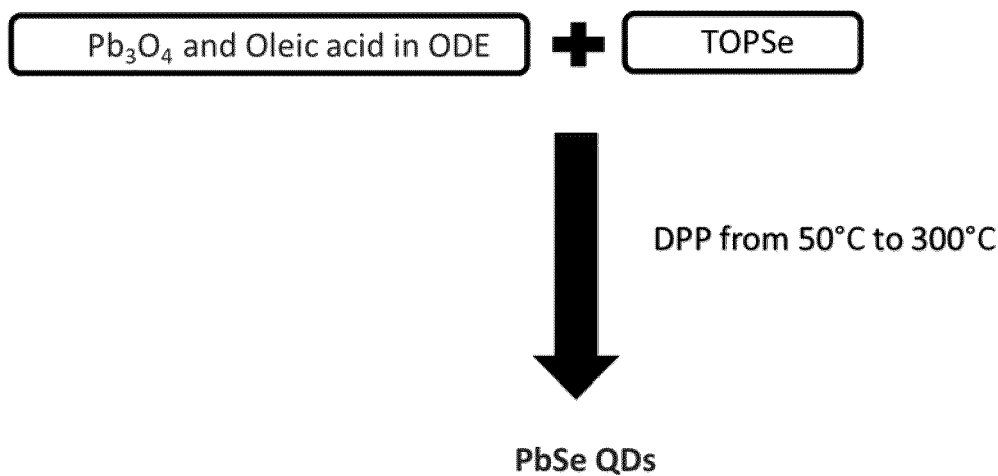
FIG. 15 shows the synthesis scheme of PbSe nanocrystals using Pb$_3$O$_4$ and TOPSe.

FIG. 15 shows the synthesis scheme of PbSe nanocrystals using Pb₃O₄ and TOPSe

Figure 16:
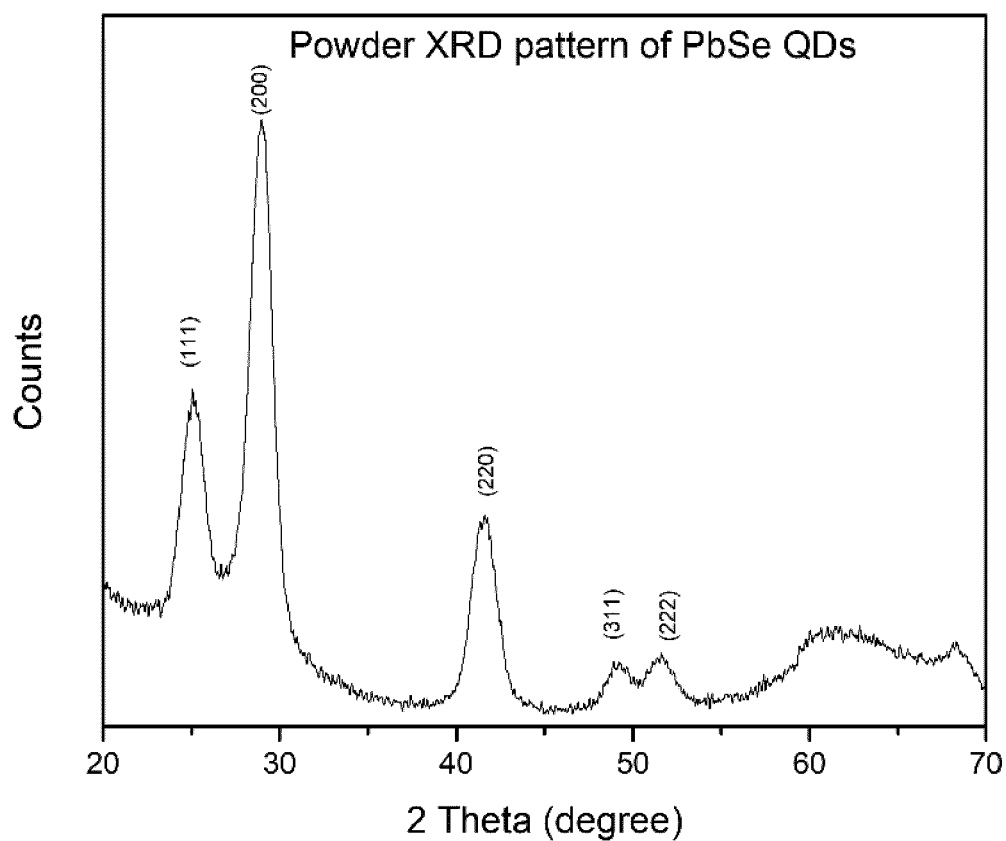
FIG. 16 shows the powder XRD pattern for the PbSe nanocrystals as prepared in Example 11.

FIG. 16 shows the powder XRD pattern for the PbSe nanocrystals prepared according to Example 11. The XRD pattern shown in FIG. 16 confirms that Example 11 produced cubic phase PbSe nanocrystals.

Figure 17:
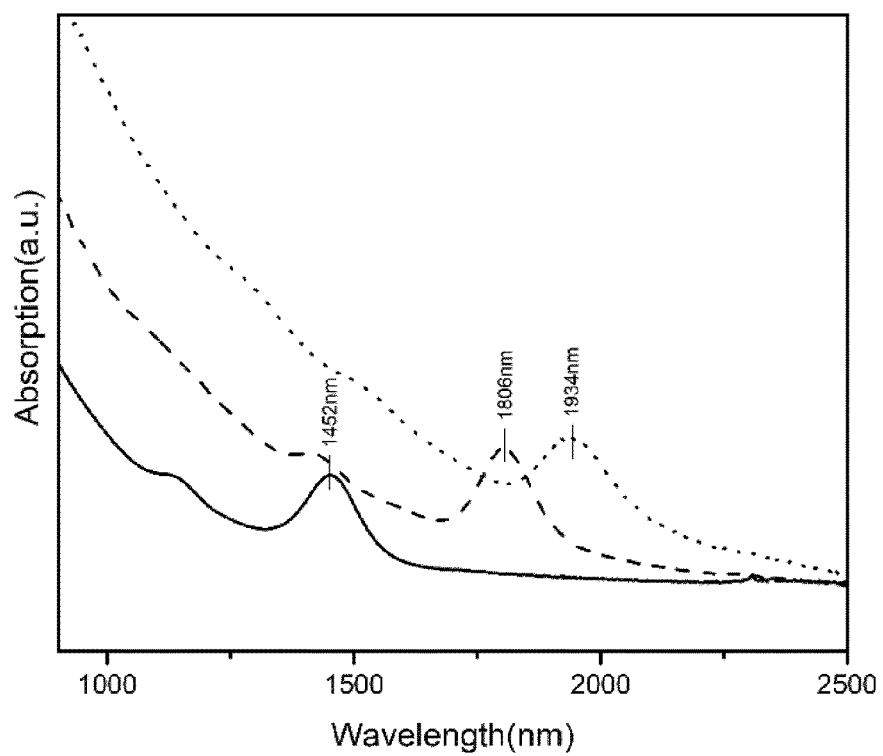
FIG. 17 shows the absorption spectra for the PbSe nanocrystals as prepared in Example 11.

FIG. 17 shows the absorption spectra for the PbSe nanocrystals prepared according to Example 11. The spectra from left to right correspond to the reaction temperature at 90° C., 100° C. and 110° C.

Table 3 shows the maximum absorption wavelength, size and composition of PbSe nanocrystals. Lower Pb to Se ratios (or increase in Se molar ratio) result in larger particles and longer maximum wavelength.

TABLE 3

| Maximum absorption wavelength $\lambda_{max}$ (nm) | Size by TEM (nm) | Pb/Se molar ratio by ICP-OES |
|---|---|---|
| 934 | 3.15 ± 0.65 | 2.91:1 |
| 1336 | 3.48 ± 0.42 | 1.84:1 |
| 2046 | 5.82 ± 0.65 | 1.62:1 |

The absorption FWHM of these nanocrystals is about 98, 87 and 100 respectively.

The molar ratio of the lead atoms (in the lead (IV) containing compound) to organic acid can be varied to achieve desired nanocrystal size and maximum absorption wavelength as shown in the PbS nanocrystal synthesis. This parameter can be applied to PbSe synthesis, but for the sake of simplicity, fixed lead to oleic acid molar ratio was used. Different Pb:Se molar ratio were also used in the PbSe synthesis. The amounts of TOPSe ranging from 1.8 g to 12.15 g correspond to Pb:Se molar ratio from 1:4 to 1:27.

Figure 18:
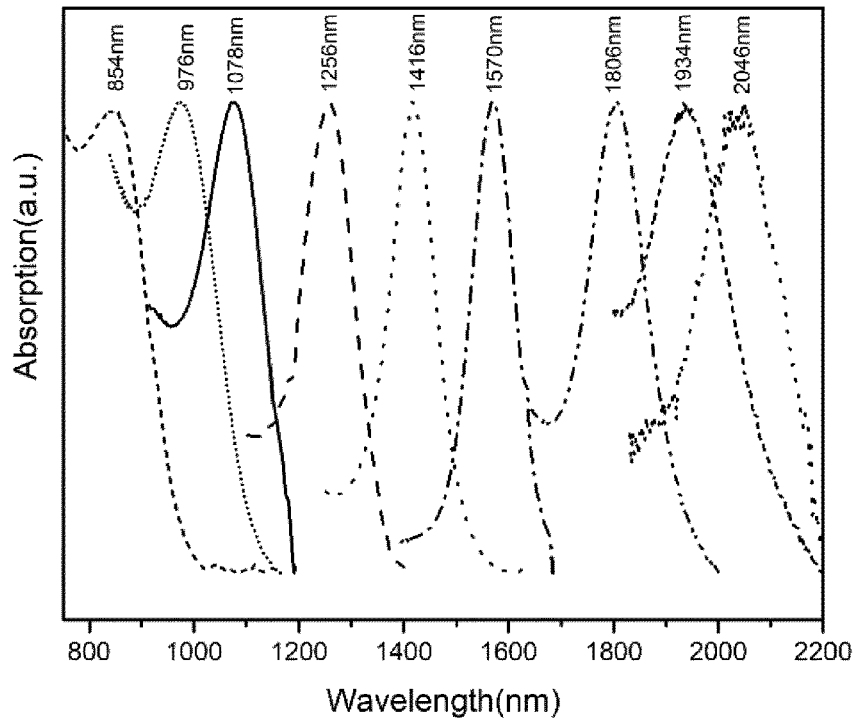
FIG. 18 shows the absorption spectra of PbSe nanocrystals demonstrating the wide spectral tunability for the PbSe nanocrystals obtained from different reaction conditions as prepared in Example 11.

FIG. 18 shows the wide spectral tunability for the PbSe nanocrystals obtained from different reaction conditions. The spectra show that maximum absorbance wavelength of PbSe nanocrystals can be controlled by using different Pb:Se ratio and different reaction temperature.

Figure 19:
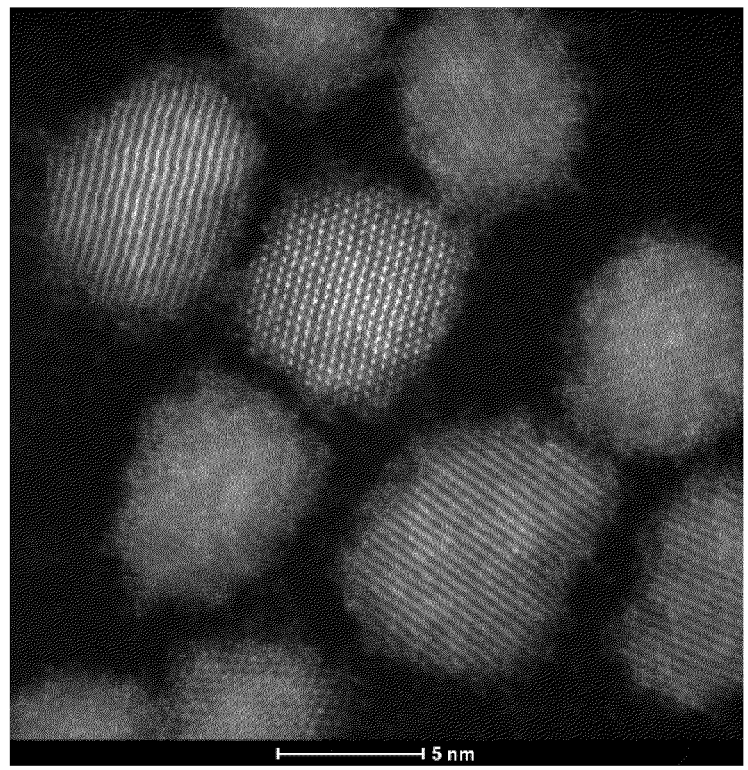
FIG. 19 shows the TEM images for the PbSe nanocrystals (($\lambda_{max}$=1926 nm) prepared from different conditions as prepared in Example 11.

FIG. 19 shows the TEM image for the PbSe nanocrystals ($\lambda_{max}$=1926 nm).

Figure 20A:
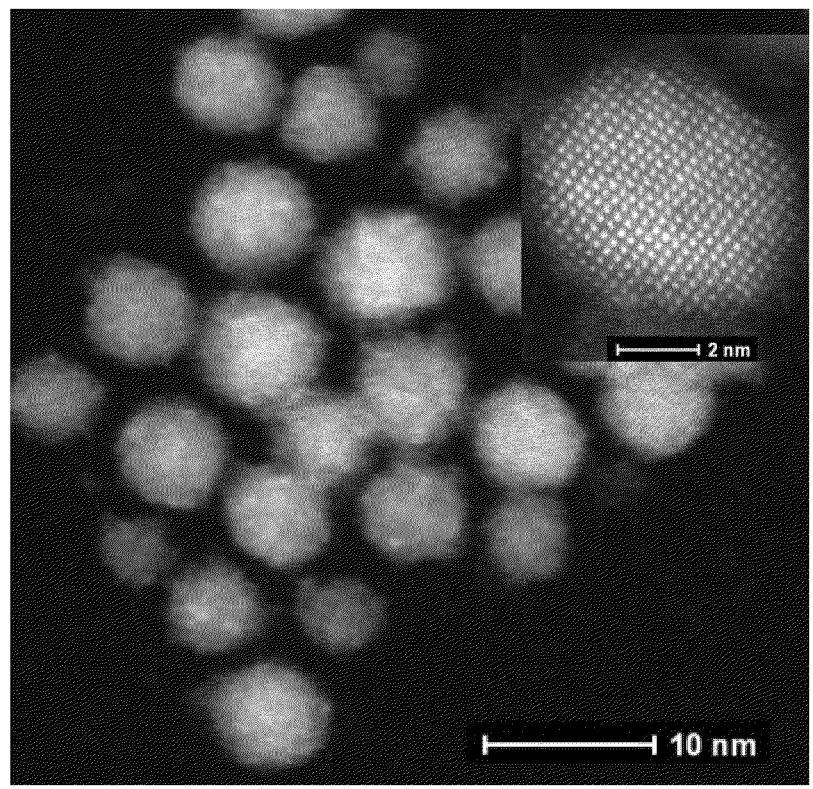
FIGS. 20a and 20b show the high resolution transmission electron microscopy (HRTEM) images of colloidal PbSe nanocrystals (($\lambda_{max}$=2046 nm) and the histogram of the particle measurement by TEM as prepared in Example 11. The PbSe dots are highly crystalline and free from stacking faults and lattice defects.
Figure 20B:
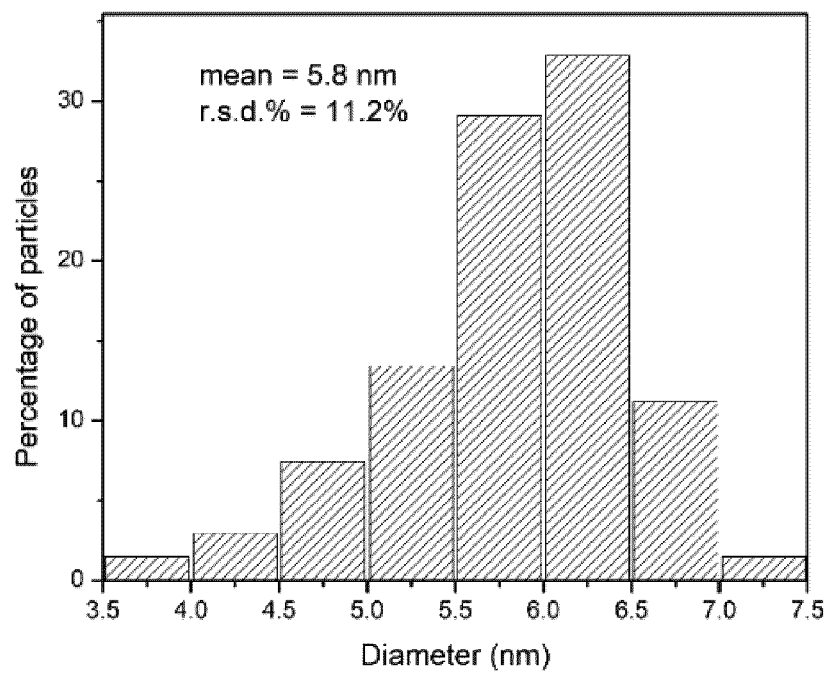

FIGS. 20a and 20b show the high resolution transmission electron microscopy (HRTEM) images of PbSe nanocrystals ($\lambda_{max}$=2046 nm) and the histogram of the particle measurement by TEM. The PbSe dots are highly crystalline and free from stacking faults and lattice defects.

Figure 21A:
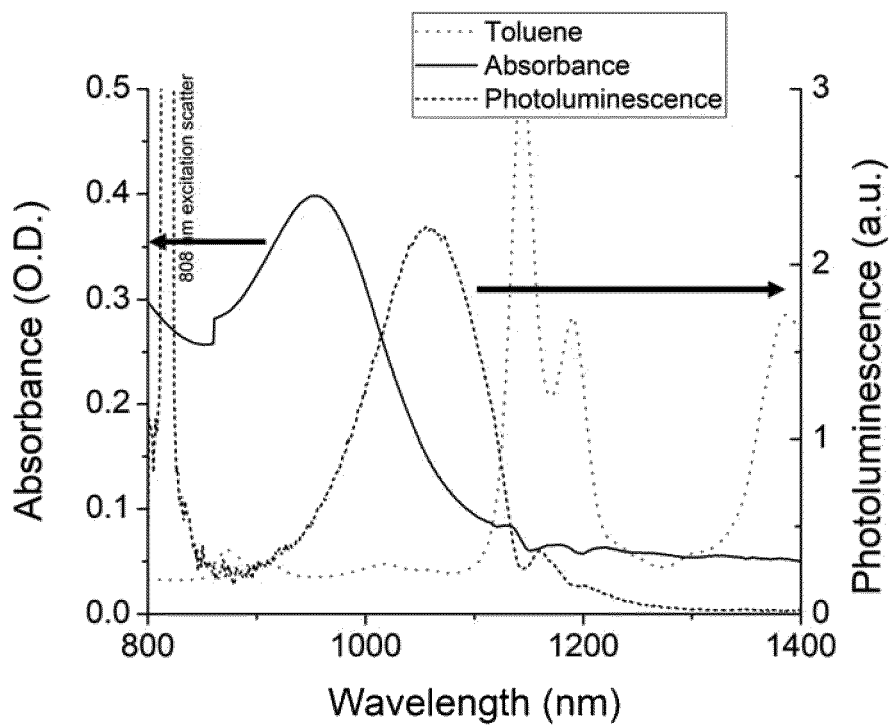
FIGS. 21a and 21b show the absorption and emission spectra of PbS nanocrystals ($\lambda_{max}$=950 nm, PL=1060±5 nm) and PbSe ($\lambda_{max}$=1000 nm, PL=1100±5 nm) as prepared in Example 6 and 11 respectively.
Figure 21B:
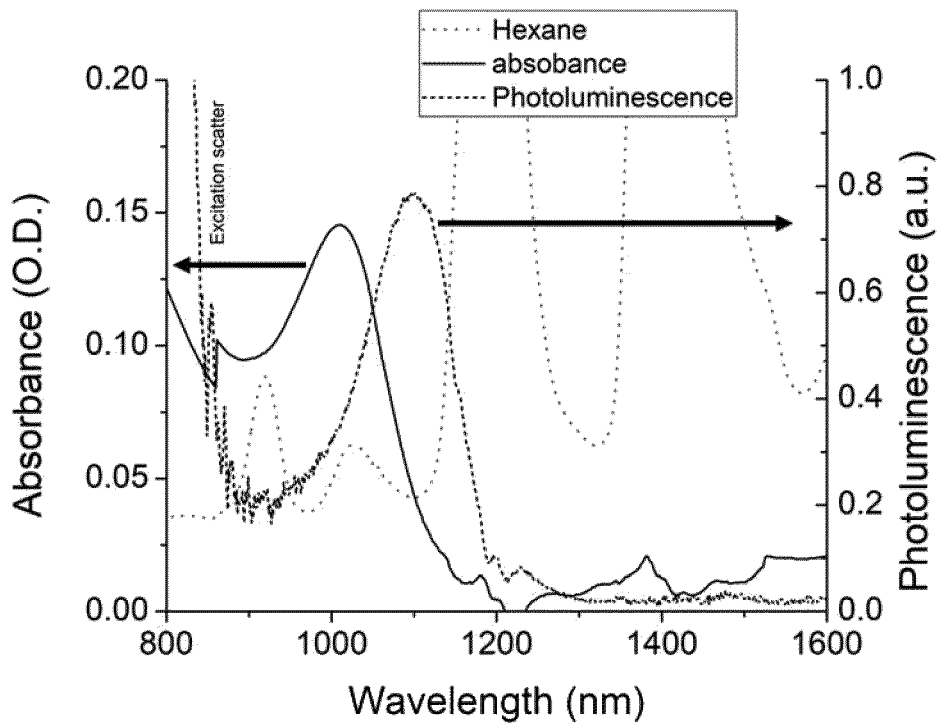

FIGS. 21a and 21b show the absorption and emission spectra of PbS nanocrystals ($\lambda_{max}$=950 nm, PL=1060±5 nm) and PbSe ($\lambda_{max}$=1000 nm, PL=1100±5 nm) as prepared in Example 6 and 11 respectively. The dots were excited with 808 nm laser.

Table 4 shows maximum absorption wavelength, photoluminescence peak, emission FWHM and quantum yield (QY) of some PbS and PbSe nanocrystals.

Photoluminescence quantum yield (PLQY) and Full Width at Half Maximum (FWHM) of some PbS and PbSe nanocrystals are shown in the Table 4.

TABLE 4

| Sample | Max absorption wavelength (nm) | Excitation wavelength (nm) | PL (nm) | Emission FWHM (nm) | QY(%) |
|---|---|---|---|---|---|
| PbSe | 1000 | 808 | 1100 ± 5 | 139 | 27 ± 2 |
| PbS | 1300 | 1064 | 1340 ± 5 | 140 | 19 ± 2 |
| PbS | 950 | 808 | 1060 ± 5 | 123 | 20 ± 2 |

PLQY data was recorded and analysed according to the methods of de Mello, J. C., Wittmann, H. F., & Friend, R. H. An improved experimental determination of external photoluminescence quantum efficiency. Adv. Mater. 1997, 9(3), 230-232; doi: 10.1002/adma.19970090308.

The spectra were recorded outside of an integrating sphere using aliquots of each sample prepared to determine the initial absorbance before preparing aliquots for PLQY. 1 ml of each sample in a glass cuvette was mounted inside a Prolite Labsphere Spectraflect integrating sphere. The samples were excited with either a THOR labs M9-A64-0200 laser diode at 1064 nm, or a THOR labs L808P200 laser diode at 808 nm. The optical power from the 808 and 1064 nm beams were 125 and 165 mW respectively. Each beam was directed through an optical chopper operating at 173 Hz before entering the integrating sphere. Emission from the sphere was focussed through a Bentham TMc300 monochromator, after which it was detected by a Newport 818-IG photodiode. Signal from the photodiode was collected using a lock-in amplifier using the chopper frequency as a reference. PLQY was determined by recording both scattered laser radiation and emitted photoluminescence for the sample, with the sample positioned both in and out of the excitation beam by means of a rotating mount. A vial of sample solvent was also recorded and its contribution to the signal removed. All data was corrected for the spectral response of the system by measurement of a Bentham IL1 halogen lamp of known spectral intensity, illumination from which was directed into the empty integrating sphere.

The invention claimed is:

1. A method for producing a lead chalcogenide nanocrystal, the method comprising contacting a lead (IV) containing compound with an organic acid and a chalcogen-containing reagent, wherein the lead (IV) containing compound is contacted with the organic acid to produce a lead salt and the lead salt is then contacted with the chalcogen-containing reagent.

2. A method according to claim 1, wherein the lead (IV) containing compound comprises lead (II, IV) oxide.

3. A method according to claim 1, which is conducted in the presence of a solvent.

4. A method according to claim 1, which comprises:
forming a first solution of the lead (IV) containing compound and organic acid in a first solvent;
forming a second solution of the chalcogen-containing reagent in a second solvent;
heating the first solution to a first temperature in the range of from 120 to 250° C. and maintaining the first solution at the first temperature for a predetermined length of time;
reducing the temperature of the first solution to a reduced temperature in the range of from 20 to 100° C.
adding the second solution to the first solution at the reduced temperature to produce a reaction mixture;
maintaining the reaction mixture at a temperature of from 20 to 300° C. for a predetermined length of time.

5. A method according to claim 1, which comprises:
forming a first solution of the lead (IV) containing compound and organic acid in a first solvent;
heating the first solution to a first temperature in the range of from 120 to 250° C. and maintaining the first solution at the first temperature for a predetermined length of time;
providing the first solution at a second temperature in the range of from 50 to 150° C.;
adding the chalcogen-containing reagent to the first solution at the second temperature to produce a reaction mixture;

maintaining the reaction mixture at a temperature of from 50 to 300° C. for a predetermined length of time.

6. A method according to claim 4, further comprising quenching the reaction mixture.

7. A method according to claim 4, further comprising purifying the lead chalcogenide nanoparticle.

8. A method according to claim 1, wherein the organic acid is a fatty acid.

9. A method according to claim 1, wherein the chalcogen-containing reagent is selected from an oxygen-, sulphur-, selenium- and tellurium-containing reagent, and mixtures thereof.

10. A method according to claim 4, wherein the chalcogen-containing reagent comprises bis(trimethylsilyl) sulphide.

11. A method according to claim 5, wherein the chalcogen-containing reagent comprises thioacetamide.

12. A method according to claim 5, wherein the chalcogen-containing reagent comprises tri-n-octylphosphine selenide (TOPSe) and diphenylphosphine (DPP).

13. A method according to claim 1, wherein the lead salt is contacted with the chalcogen-containing reagent at a temperature of from 20 to 100° C.

14. A method according to claim 1, wherein the lead salt is contacted with the chalcogen-containing reagent at a temperature of from 50 to 300° C.

15. A method according to claim 1, comprising the step of modifying a reaction condition so as to control the size of the nanocrystal prepared.

16. A method according to claim 15, wherein the reaction condition to be modified comprises one or more of the following:

(i) solvent type;
(ii) amount of solvent;
(iii) organic acid type;
(iv) amount of organic acid;
(v) mode of addition of the reactants;
(vi) reaction temperature;
(vii) reaction time
(viii) ratio of Pb to chalcogen-containing reagent; and
(ix) addition of a secondary solvent.

17. A method according to claim 1, comprising monitoring an optical property so as to monitor the progress of the production of the nanocrystals.

18. A method according to claim 17, wherein the optical property is a UV-visible-near infrared absorbance spectrum.

19. A method according to claim 3, wherein the solvent comprises a non-polar solvent or a polar solvent.

20. A method according to claim 19, wherein the non-polar solvent is octadecene.

21. A method according to claim 19, wherein the polar solvent is selected from the group consisting of DMF, NMP, DMAc, THE, and acetone.

22. A method according to claim 6, wherein the reaction mixture is quenched by adding a quenching solvent to the reaction mixture.

23. A method according to claim 8, wherein the organic acid is oleic acid.

24. A method according to claim 13, wherein the lead salt is contacted with the chalcogen-containing reagent at a temperature of from 30 to 60° C.

25. A method according to claim 14, wherein the lead salt is contacted with the chalcogen-containing reagent at a temperature of from 50 to 180° C.

* * * * *